United States Patent
Richaud et al.

(12)

(10) Patent No.: US 6,197,590 B1
(45) Date of Patent: *Mar. 6, 2001

(54) PROCESS FOR INTEGRATION OF A CHOSEN GENE ON THE CHROMOSOME OF A BACTERIUM OBTAINED BY THE SAID PROCESS

(75) Inventors: Francois Richaud; Bruno Jarry, both of Paris; Koïchi Takinami, Malabry; Osamu Kurahashi; Anne Beyou, both of Paris, all of (FR)

(73) Assignee: Eurolysine, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/941,122

(22) Filed: Sep. 30, 1997

Related U.S. Application Data

(63) Continuation of application No. 08/436,113, filed on May 8, 1995, now abandoned, which is a continuation of application No. 08/341,460, filed on Nov. 17, 1994, now Pat. No. 5,595,889, which is a continuation of application No. 07/859,610, filed on Mar. 23, 1992, now abandoned, which is a continuation of application No. 07/313,625, filed on Feb. 21, 1989, now abandoned.

(51) Int. Cl.[7] .................................................. C12N 15/74

(52) U.S. Cl. ...................... 435/473; 435/476; 435/252.3; 435/252.33; 435/488

(58) Field of Search .............................. 435/5, 6, 30, 74, 435/39, 69.1, 172.1, 172.3, 252.3, 252.8, 320.1, 243, 471, 473, 476, 252.33, 488; 935/29, 31, 36, 42, 55, 56, 57, 58, 72, 73, 79, 80

(56) References Cited

PUBLICATIONS

Neidhardt, F (1987), E. coli and S. typhimurium, vol. 2–pp. 1071–1109.*
Gramajo, H. et al (1988). Gene 65, 305–314.*
Parsot, C. (1986). The Embo Journal 5, 3013–19.*
Maniatis, T. et al (1982) In Molecular Cloning A Laboratory Manual; Cold Spring Harbor Press, NJ. pp. 403–434.*

* cited by examiner

*Primary Examiner*—Remy Yucel
(74) *Attorney, Agent, or Firm*—Cooley Godward LLP

(57) ABSTRACT

The present invention relates to a process for integration of a chosen gene or of a specific DNA sequence in a DNA sequence such as the chromosome or episome of a bacterium, wherein:
a) the said chosen gene or the chosen DNA sequence is cloned inside a defective transposon outside the essential parts of the transposon,
b) the said transposon is integrated in the DNA sequence such as the chromosome or the episome of the said bacterium,
and also the bacterium strains obtained by implementation of this process.

44 Claims, 18 Drawing Sheets

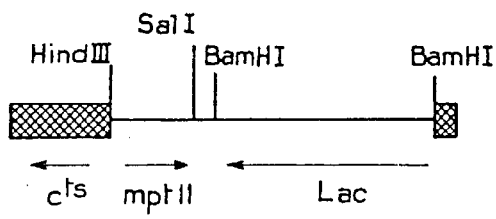
FIG_1
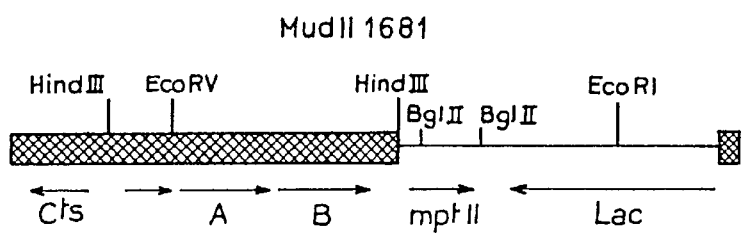
FIG_2
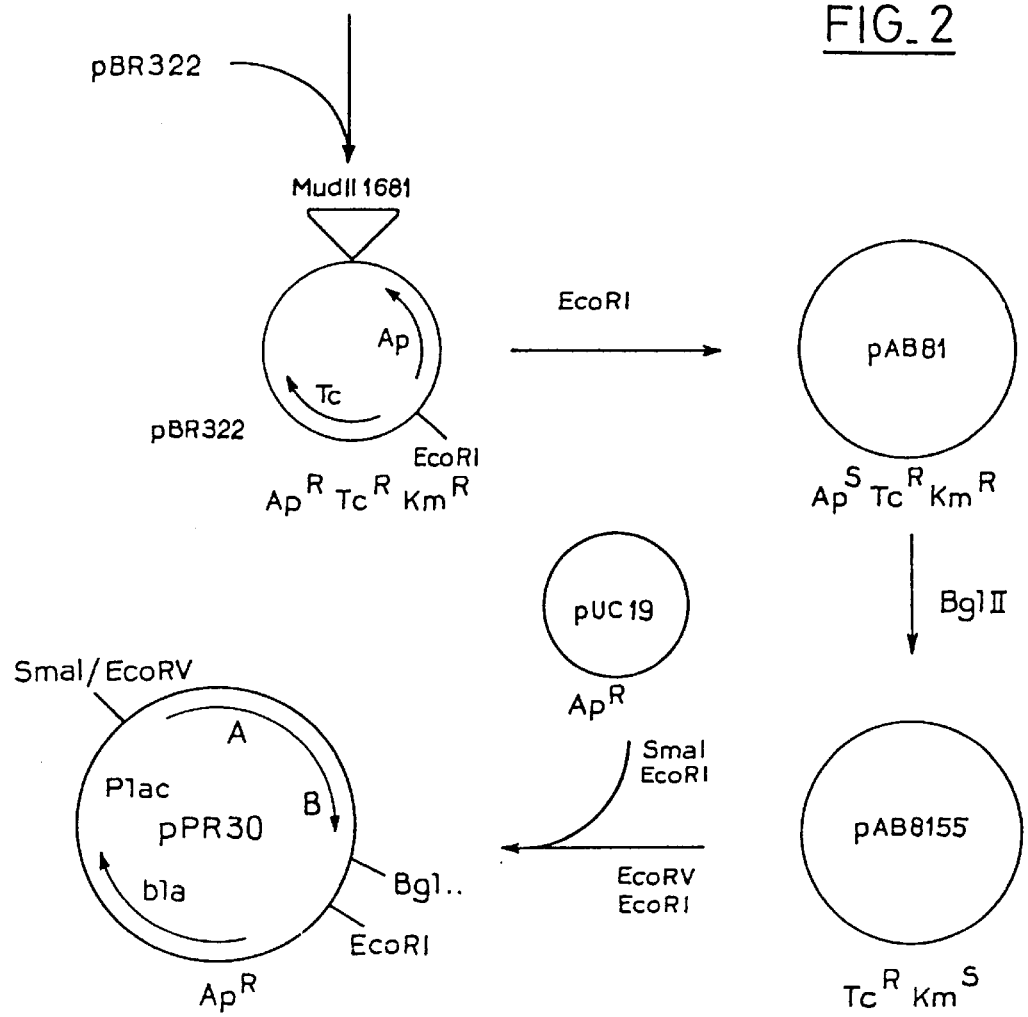

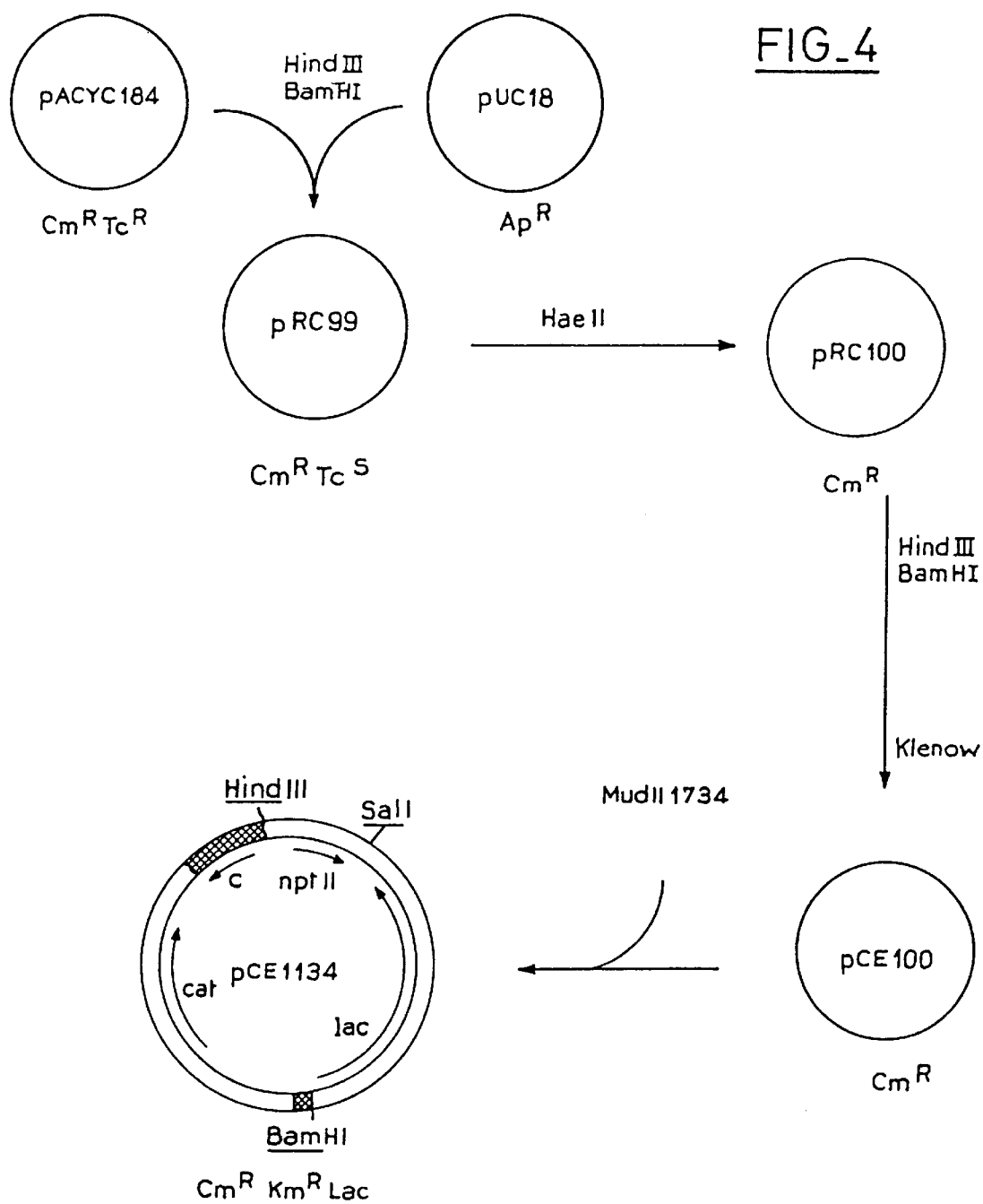
FIG_4

FIG_5
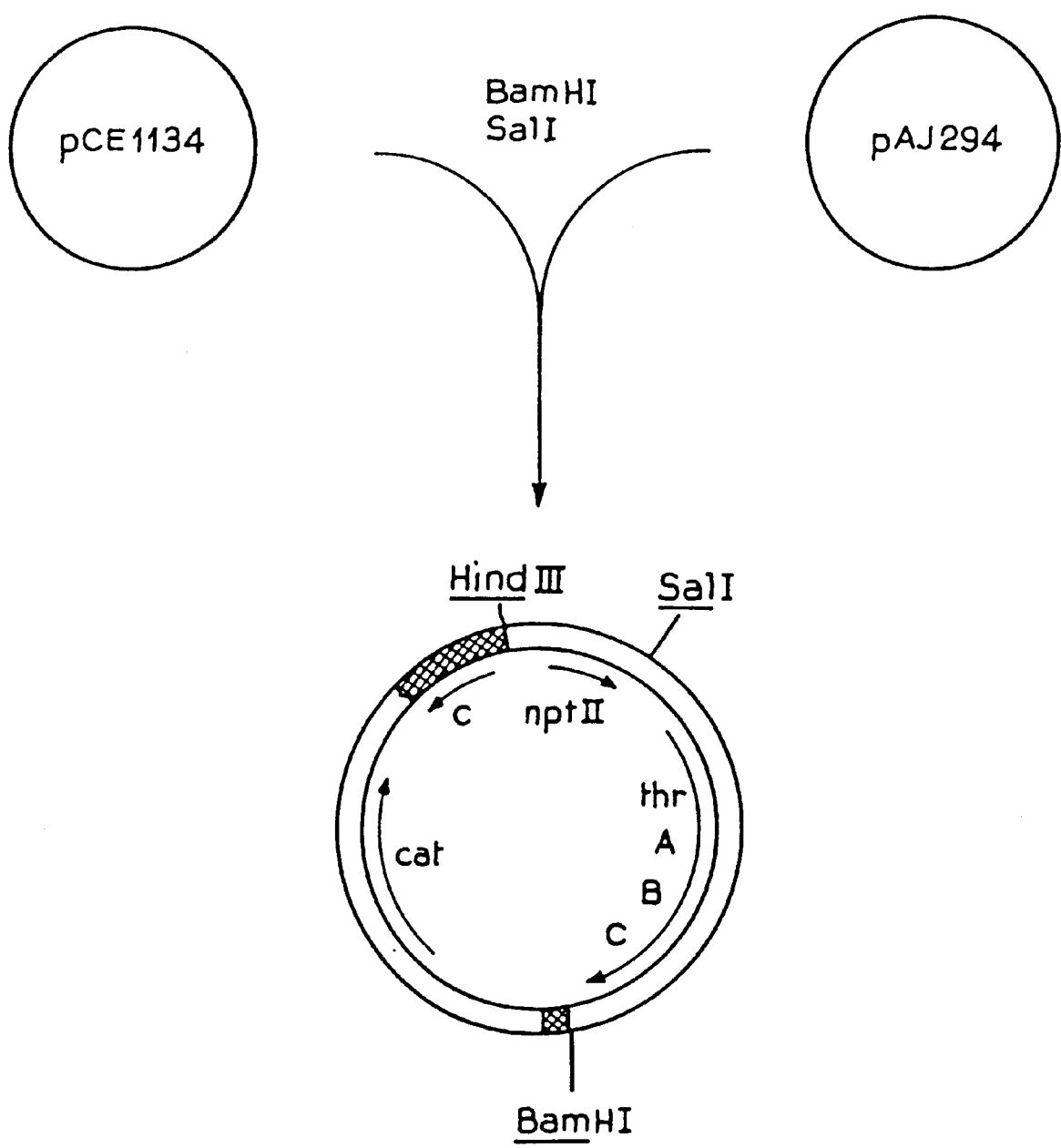

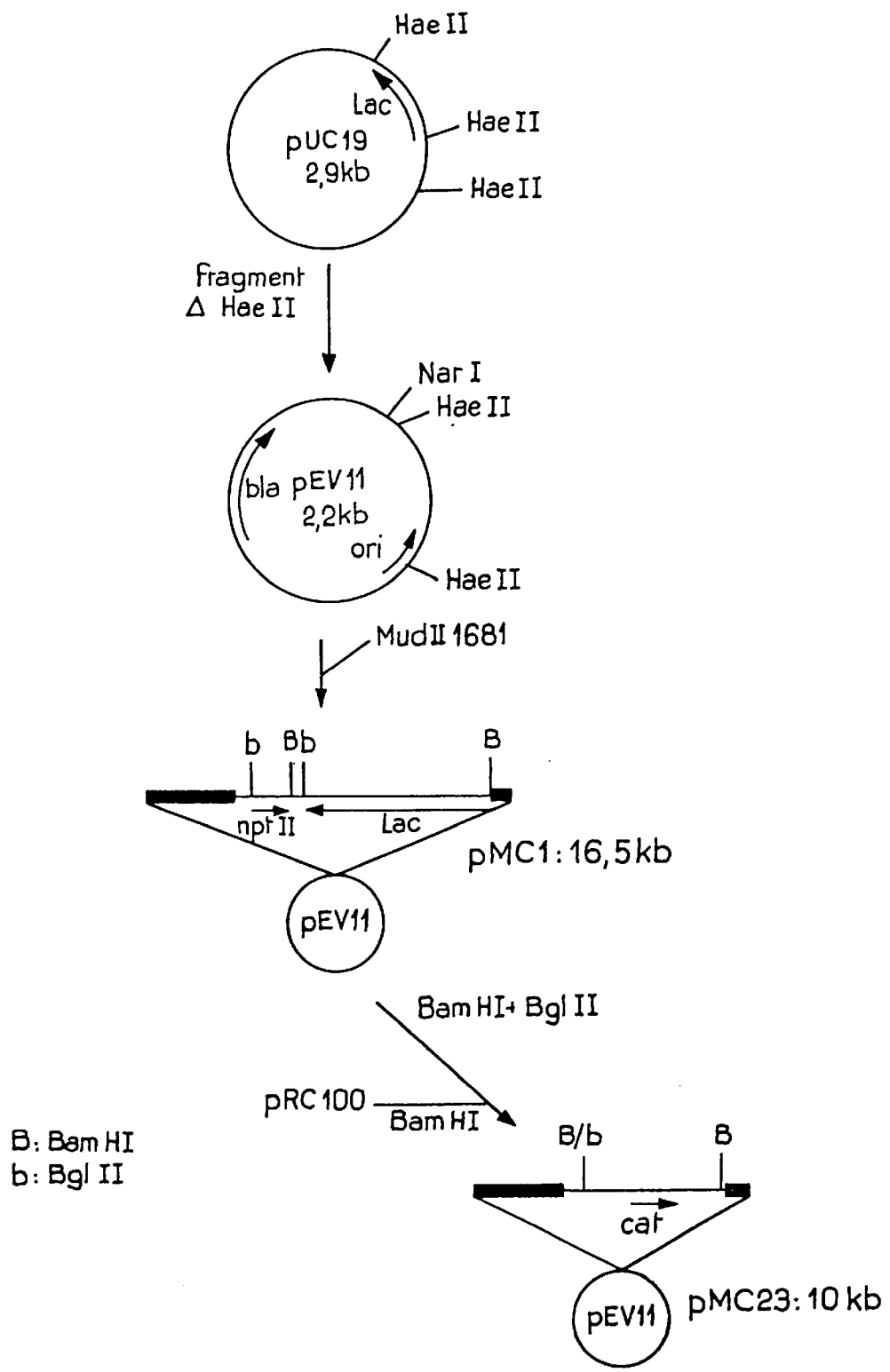
FIG. 7: Construction of pEV11, pMC1 et MC23

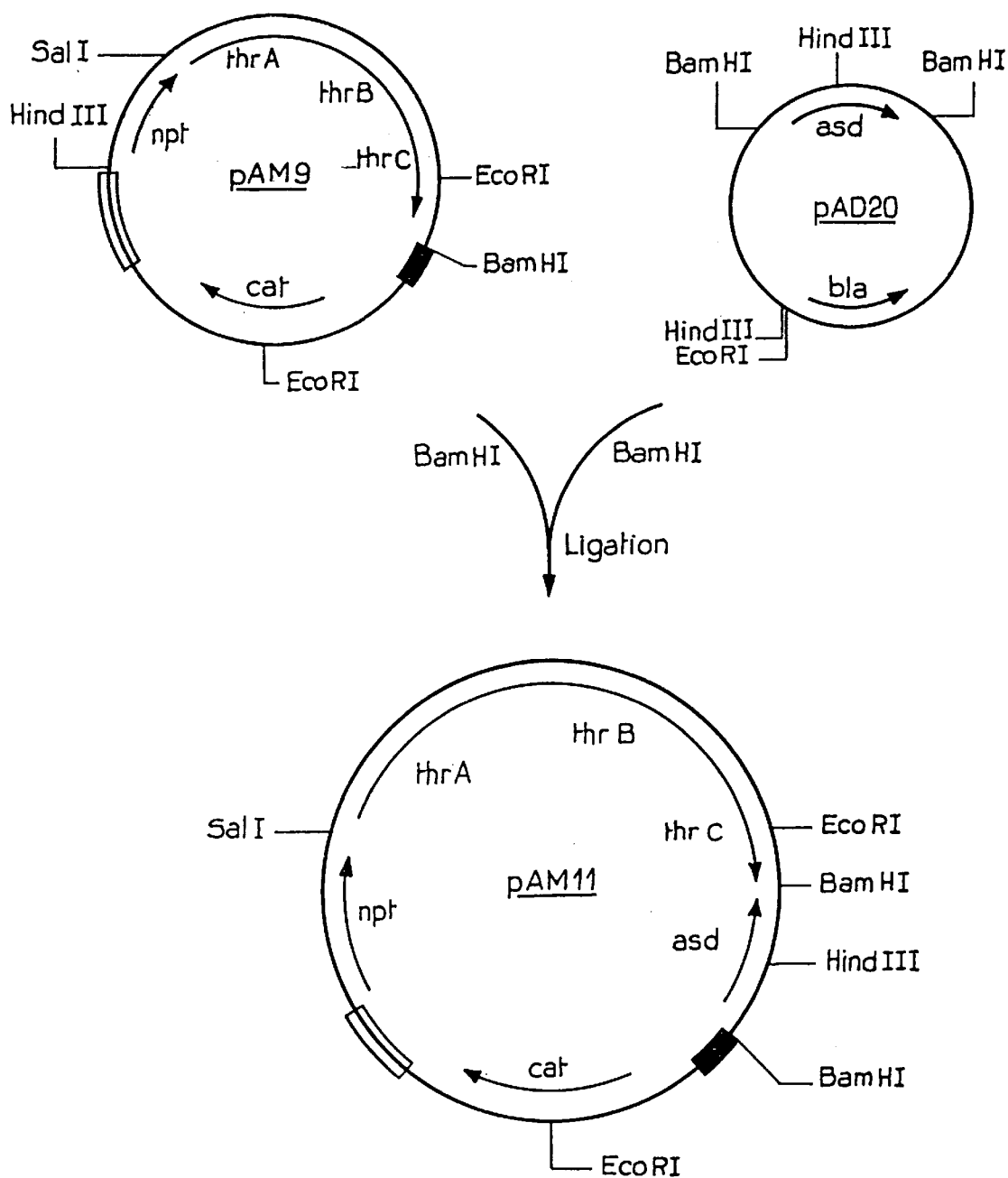
FIG_12
Construction of the pAM11 plasmid containing the asd gene and the threoning operon

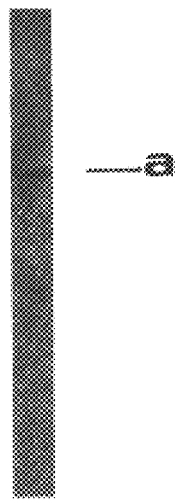 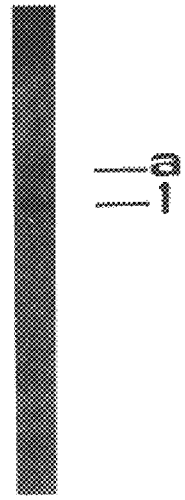 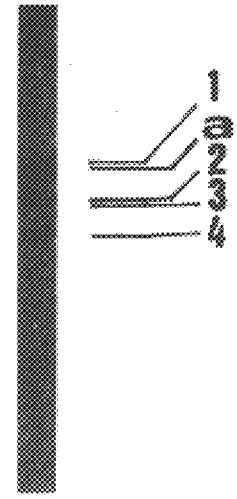
FIG.15A   FIG.15B   FIG.15C
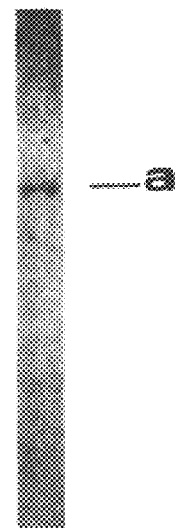 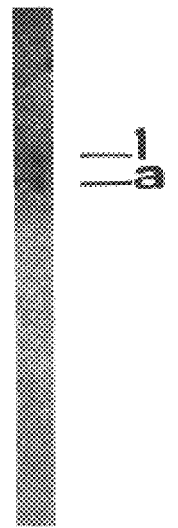 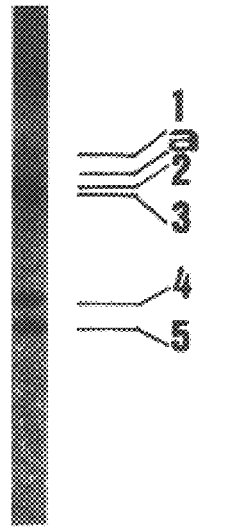
FIG.16A   FIG.16B   FIG.16C Cloning of the aspA gene in a defective phage

PROCESS FOR INTEGRATION OF A CHOSEN GENE ON THE CHROMOSOME OF A BACTERIUM OBTAINED BY THE SAID PROCESS

CROSS REFERENCE TO RELATED APPLICATIONS

This application is a Continuation of U.S. application Ser. No. 08/436,113, filed May 8, 1995 now abandoned, which is a continuation of U.S. application Ser. No. 08/341,460, filed Nov. 17, 1994 now U.S. Pat. No. 5,595,889, which is a continuation of U.S. application Ser. No. 07/859,610, filed Mar. 23, 1992 now abandoned, which is a continuation of U.S. application Ser. No. 07/313,625, filed Feb. 21, 1989 now abandoned.

BACKGROUND OF THE INVENTION

The present invention relates to a new method for the amplification and stabilization of the copy number of chosen genes in a microorganism.

The invention is illustrated by means of examples given hereinafter in which the sequence coding for an enzyme, beta-galactosidase, and the genes coding for three enzymes involved in the biosynthesis of L-threonine are transferred inside the chromosome of a microorganism.

These genes have been shown to be stably fixed in the chromosome. The resulting strains are therefore better producers of, in the first instance, the corresponding enzymes or, secondly, of L-threonine amino acids, than are the parental strains.

The bacteria are capable of synthesizing useful active principles such as enzymes and amino acids. The production by fermentation involves complex biochemical procedures controlled by multiple genes and gene products. The products of the fermentation are obtained in relatively small quantities. In order to improve this production by fermentation, it would be useful to increase the number of copies of the genes involved, in a manner such that the number of these copies could be controlled and stabilized in the chromosome or the episomes of the microorganism.

Several methods have been described in the scientific literature in which the copy number of a gene can be amplified in a microorganism, in particular by means of circular plasmid vectors. However, the number of copies obtained by these methods is extremely variable and depends on the particular vector, the length of the chosen gene and the particular physiological conditions of the microorganism. None of these methods are concerned with the amplification of the gene to a chosen level, avoiding an unnecessary excess of copies, and this with a stable fixation of these copies in the chromosome.

Various documents suggest the use of transposons as vectors in bacteria or other organisms, in particular:

U.S. Pat. No. 4,670,388,

EP-A-0,200,708

EP-A-0,091,723

GENE, vol. 42 (1986), pages 185–192

THE EMBO JOURNAL, vol. .4, No. 4, 1985, pages 891–898, and 5 BIOTECHNOLOGY, vol. 4, No. 5, May 1986, pages 446–449, New York, US.

However, none of these documents describes a process by which it is possible to obtain a stable integration of a specific DNA sequence with a defined copy number.

SUMMARY OF THE INVENTION

One aim of the invention is to describe a method for amplifying and stably fixing the copies of chosen genes in a microorganism with more flexibility and more reliability than was hitherto possible. This aim as well as other objects of the invention, such as are envisaged hereafter, have been accomplished, for example, by providing the *Escherichia coli* bacterium with a transposable element having a wide host range and derived from the Mu phage, and in which the genes of the transposase cannot be expressed or are deleted. Such a transposon is a defective transposon. Under particular reversible genetic conditions which are easy to reproduce for organisms of the same genus or of a different genus, this transposon and the genes which can be introduced into it by genetic engineering technology can be made to multiply inside the chromosome of the microorganism. When the particular genetic conditions are removed, the various copies of the transposon remain fixed in a stable manner inside the chromosome.

The present invention relates to a process for integration of a chosen gene or of a specific DNA sequence (inside a bacterium) in a DNA sequence such as a chromosome or an episome, wherein:

a) the said chosen gene or the chosen DNA sequence is cloned inside a defective transposon outside the essential parts of the transposon, b) the said transposon is integrated in the DNA sequence inside the bacterium.

More particularly, the process according to the invention is used to amplify the chosen copy number of genes in order to obtain a specific number of copies. In this case the process according to the invention is a process for integration of a specific number of copies of a chosen gene or of a specific DNA sequence in a DNA sequence such as the chromosome or episome of a bacterium, wherein:

a) the said chosen gene or the chosen DNA sequence is cloned inside a transposon outside the essential parts of the transposon, the said transposon being defective, b) the said transposon is integrated in the DNA sequence such as the chromosome or the episome of the said bacterium, c) the said defective transposon is complemented so as to be able to transpose several times and the complementation is then stopped after a specific number of transpositions.

According to the invention any transposon can be used which transposes inside any site in the bacterial DNA.

In the present text the term "transposons" is intended to mean both "true transposons" and also phages having the capacity to transpose.

Preferred transposons are Tn3, Tn5, Tn7, Tnl0, Tn903, TnHoHo, IS 1, IS 10, IS 50 and the MudI and MudII phages. The MudI and MudII phages are particularly preferred.

The use of defective transposons, which are transposons incapable of transposing by themselves, makes it possible to obtain a stable integration. For such a use the transposons used have no genes for the transposase or these genes are not active in the said bacterium. A transposon is very particularly preferred which lacks genes coding for the transposase, but it is also possible to use a transposon in which the trans-acting transposases are repressed or inactive under normal conditions.

According to the invention it is possible to use any bacterium in which the transposons described hereinabove can transpose.

The preferred bacteria are members of the Enterobacteriaceae family, for example *Escherichia coli, Citrobacter freundii, Erwinia herbicola* or *E. chrysanthemi, Salmonella thyphimurium, Shiaella soneii, Enterobacter cloacae, Serratia marcescens* or members of the Rhizobiaceae family, such as *Agrobacterium tumefaciens* or members of the Pseudomonas family, such as Pseudomonas putida for example.

By the term chosen gene there is understood a gene which is not normally present in the said transposon or which is not present in the host bacterium.

As chosen gene there may be used a cloned gene or a hybrid gene, a gene segment or a synthesized gene. The gene can be expressed in the host bacterium and may be of animal, vegetable or microbial origin. Several genes can be inserted in the transposon.

The chosen gene can be under the control of a promoter which is itself inside the transposon and which ensures the expression of the said gene in the said bacterium.

The cloned genes are inserted by known genetic engineering techniques or according to the process described hereinbelow.

For convenience sake, it is simpler to start from a plasmid containing the defective transposon. The transposon is made defective by deletion or mutation.

The plasmid containing the transposon is isolated from the bacterium and cleaved with appropriate restriction enzymes. The chosen genes are also extracted from their host and then purified after cleavage by means of restriction enzymes. The cloning of a marker gene such as an antibiotic-resistant gene (not for example) or another "reporter" gene (lacz for example) at the same time as the inserted genes is preferable for the selection of the transposition events. The number of transpositions is evaluated by determination of the expression of the marker gene. The said expression of the marker gene can be determined by the resistance to an antibiotic when the marker gene is an antibiotic-resistant gene; the expression of the marker gene can also be determined by the, coloration of a substituent when the marker gene codes for an enzymatic activity which can be evaluated by a colorimetric assay. The various fragments are recombined by ligation in vitro and transformed in the appropriate recipient bacterium. The transformants are selected and then analyzed in order to establish that the structure is suitable. The resulting composite defective transposon can be placed in other strains by transformation or transduction. Conventional genetic engineering methods are described in "Molecular cloning, a laboratory manual" (Maniatis et al., Cold Spring Harbor Laboratory, New York, 1986).

When the process of the invention is also used to amplify the number of copies of the chosen gene, the integration of a specific number of copies of the said chosen gene, during the process described hereinabove using a defective transposon and after integration, the said transposon incapable of transposing is complemented in order to be able to transpose several times, and the complementation is then stopped after a specific number of transpositions.

The said complementation can be carried out in various ways. If the transposon is truly defective, that is to say if it does not possess any transposase, the latter can be introduced into the host cell by means of a plasmid or a phage coding for the said transposase.

If the expression of the transposase is repressed, it is possible to inactivate the repressor. In the case of a repressor sensitive to heat an increase in temperature will result in the expression of the transposase.

Once inserted in the recipient DNA, the transposon produced can be amplified by transposition onto the genome by means of inactivation of the repressor leading to expression of the genes of the transposase.

The transposon in which the transposase genes are lacking can be amplified by introduction of a plasmid or a phage containing trans-acting transposase genes.

When the complementation is effected by introduction of an extra-chromosomal element, such as a plasmid or phage especially, this complementation can be effected at the same time as the integration stage.

The amplified transposons are maintained in a stable manner in the bacterial DNA under the normal culture conditions. It is preferred to use a defective to transposon to stabilize the chosen genes. Any DNA whatsoever in a bacterial cell can be the transposition target. DNAs are very particularly preferred which are maintained in a stable manner in the bacterial cell such as the chromosome or a stable plasmid.

According to a preferred embodiment of the invention the defective transposon used is MudII1734 (Castilho et al., J. Bact., 158, 488, 1984) which is present as a defective prophage in an *E. coli* strain (POII1734) already lysogenic for a Mucts mutant phage. This strain, cultured at low temperature, is briefly heated and the resulting lysate is used for the transduction with a suitable recipient strain. The bacteria which are resistant to the appropriate antibiotic and which do not produce any Mucts phage only contain the transposon in their chromosome.

The MudII1734 is inserted on a plasmid, and the inside of the Mud can then be modified (according to the above part of the description page 3, line 37 to page 4 line 16).

The plasmid containing the modified Mud is transformed in a strain lysogenic for Mucts. The phage lysate is obtained after increasing the temperature. This phage lysate is used to transduce the modified Mud on the chromosome of a specific bacterium.

In order to amplify the modified Mud, the strain which carries the defective transposon on its chromosome is transformed with a plasmid which contains the two transposase genes, namely genes A and B, or is infected by the Mu phage.

In the case of amplification by a plasmid, the plasmid containing the A and B genes is maintained in the bacterium by use of a (antibiotic-resistant) selection. The bacteria which grow in the presence of this antibiotic and at the same time synthesize in large quantity the product of a gene situated in the transposon are selected. The bacteria which express these two phenotypes can contain several additional copies of the transposon on their chromosome.

The bacteria which have lost the plasmid and which are not lysogenic for the phage can be obtained naturally.

The determination of the transposon copy number can be carried out by selection of the bacteria described hereinabove according to the level of expression of a marker gene in the transposon.

The number of copies of the transposon containing an antibiotic-resistant gene can be estimated according to the resistance of the bacterium to the antibiotic.

The number of copies of the transposon including the lac operon can be estimated according to the intensity of the coloration of bacterial colonies after degradation of a substrate such as X-gal (5-bromo-4-chloro-3-indolyl-beta-D-galactoside).

The number of copies of the transposon can be determined using Southern blotting and DNA—DNA hybridization techniques with appropriate probes.

The chosen genes amplified by means of the transposon remain stable insofar as the transposase genes are not present or are inactive in the bacterial strain.

To this end it is also preferable to introduce into the host bacterium, after amplification, DNA polymerase I or 5'-3' exonuclease mutations or an HU deficient mutation.

An important aspect of this invention is that the strains obtained are very stable. The defective transposon can neither transpose further nor be deleted by any efficient mechanism. After a culture for many generations without selective pressure, the defective transposons still occupy the same position in the chromosome.

Moreover, no transfer of the defective transposon is detectable in cocultivation experiments.

The present invention also relates to the said bacterium which can be obtained by the process according to the invention and likewise relates to a process for the preparation of the product of the heterologous gene comprising the culture of the bacterium according to the invention in a suitable culture medium and the recovery of the said product.

Although the chosen gene can code for a peptide or a protein having a therapeutic or industrial use, one of the implementations of the process concerns the preparation of metabolites by using the bacterium obtained according to the process described hereinabove using a defective transposon containing one, several or all of the genes for the biosynthesis of the metabolites.

Among the genes of industrial interest, there should be mentioned genes coding for the biosynthesis of amino acids, in particular threonine or for the biosynthesis of vitamins, such as biotin. However, the amplification of the expression of certain enzymes may also permit an overall super-expression of certain metabolites, the examples showing the super-expression of the asd gene and the aspA gene.

The process according to the invention is very versatile and can be used to amplify any type of DNA sequence.

The bacterium thus obtained, having the capacity to produce one or several enzymes, or one or several amino acids or desired products can be cultured in much the same way as usual. Ordinary culture media are used containing carbon sources, nitrogen sources, inorganic ions and, if required, organic micronutrients such as amino acids and vitamins. Suitable carbon sources include glucose, sucrose, lactose, starch hydrolysate containing these sugars, whey and molasses. Preferred sources of nitrogen include ammonia gas, ammonia water and ammonium salts. Culturing is carried out under aerobic conditions at a controlled pH and temperature until the cells in practise cease to produce the desired product. For a production such as that of an amino acid or a protein, the strain which already produces the desired product is preferable as a host strain for the envisaged production.

The following examples and the figures will illustrate other characteristics and advantages of the present invention.

BRIEF DESCRIPTION OF THE DRAWINGS

FIG. 1: diagrammatically represents the restriction map of the MudII1734 transposon with a wide host range.

FIG. 2: diagrammatically represents the construction and the restriction map of the pBR322 (MudII-1681) and pPR30 plasmids.

FIG. 4: diagrammatically represents the construction and the restriction map of the pCE1134 plasmid.

FIG. 5: diagrammatically represents the construction and the restriction map of the pAM9 plasmid.

FIG. 7: diagrammatically represents the construction of pEV1l, pMC1 and pMC23.

FIG. 12: shows the construction of the pAM11 plasmid containing the asd gene and the threonine operon.

FIGS. 13 to 16: show the results of electrophoresis followed by blot hybridization of the DNA of strains EL1016, EL1012 and EL1013 for lanes A to C respectively.

In FIG. 15 the chromosomal DNAs are digested by SalI and hybridized with the BamHI fragment, containing the asd gene, of pAN11 as the probe.

In FIG. 16 the chromosomal DNAs are digested by EcoRI and hybridized with the BamHI fragment, containing the asd gene, of pAM11 as the probe.

DETAIL DESCRIPTION

EXAMPLE 1

Figure 3:
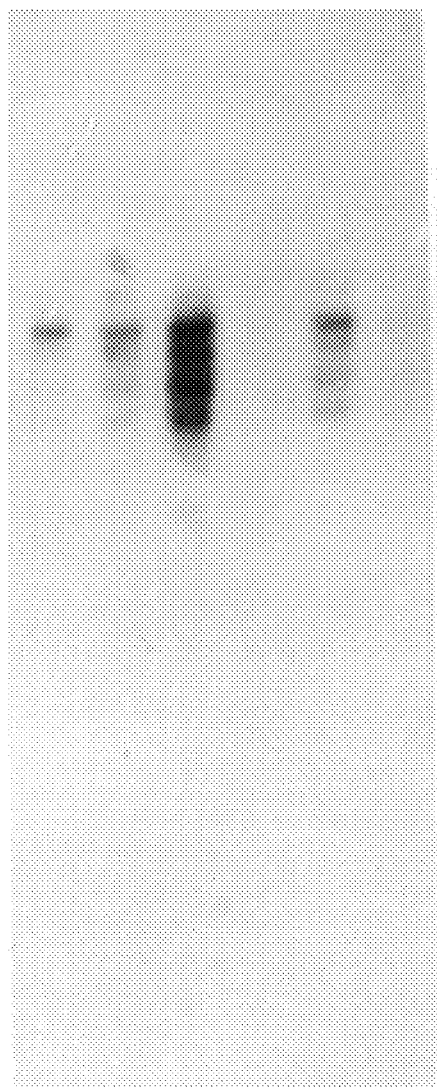
FIG. 3: shows the results of electrophoresis followed by the blot hybridization of:
DNA from a strain in which the copy number of the transposon has been amplified (lane f),
DNA from 5 strains isolated after 170 generations (lanes a to e), (the probe is pCE1134; the DNA was digested by EcoRI).
Figure 6A:
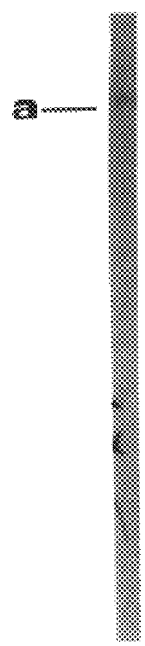
FIGS. 6A–6D: shows the results of electrophoresis followed by blot hybridization of the DNA of strains AJ11332, EL1001, EL1002, and EL1003 respectively for lanes A to D; (the probe is a small EcoRI fragment of pAM9; the DNA of the strains was digested by EcoRI).
Figure 6B:
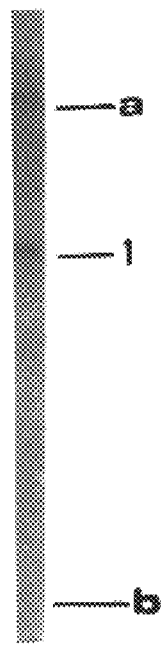
Figure 6C:
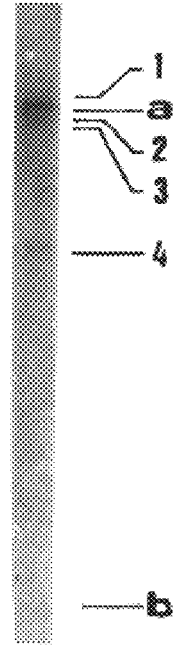
Figure 6D:
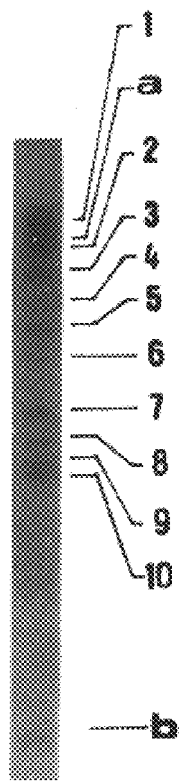

Production of an Enzyme Having a Beta-Galactosidase Activity by Amplification of the Coding Region Responsible for the Production by Fermetation of Beta-Galactosidase Preparation of a strain containing in its chramosome one additional copy of the beta-galactosidase gene cloned inside a defective transposon The *E. coli* strain POII1734 s F⁻, araD139, ara :: (Mucts 3, Δ (lac)X74), galU, galK, rsL (Sm$^R$), (MudII1734) containing MudII1734 (FIG. 1) (Castilho et al., J. Bacteriol., 158, 488, 1984) was cultured in 2 ml of LB medium for 2 hours at 30° C., was subsequently subjected to thermal shock at 45° C. for 15 minutes, and was then cultured at 37° C. for 2 hours, this leading to a phage lysate. In order to obtain the phage solution, this lysate was mixed with several drops of chloroform and subsequently centrifuged. The supernatant was used as phage solution to infect the bacterial strain.

The *E. coli* strain MC4100 : F-araD139, Δ(argF-lac, U169, psL150, relA1, flbS301, DtsF25, deoCl (Casabadan, 1975) such as described by Castilho et al. (1984) was cultured overnight in LB medium. CaCl$_2$ and MgSO, were subsequently added, giving a final concentration of 1 mM and 2.5 mM, respectively. 200 μl of this culture and of the phage solution described hereinabove were mixed and left at room temperature for 15 minutes. After addition io of 2 ml of LB medium and incubation for 2 hours at 30° C., this cell suspension was spread on a dish of LB medium containing 20 pg/ml of kanamycin (Km) and 10 mM of X-gal and subsequently incubated for 24 hours at 30° C. in order to select the transductants.

The colonies not producing Mucts after checking by spreading the replicas on a layer of *E. coli* sensitive to Mu were identified and one strain MC4100 (MudII1734) was retained. This strain does not produce beta-galactosidase, as shown by the white color of the colonies on the dishes of LB medium supplemented with X-gal, a substance which changes from colorless to blue when it is hydrolyzed to beta-galactosidase.

The DNA was extracted, cut with the EcoRI restriction enzyme and the fragments obtained were separated on a gel and blotted on nitrocellulose. After hybridization with the DNA of the labeled transposon, two bands were visible on the resulting autoradiogram indicating the presence of a copy of the transposon in the strain.

Cloning of the A and B transposase genes of the Mu phage on a multicopy plasaid

The DNA extracted from the plasmid pAB8155 containing the defective phage MudII1681 was cut with the EcoRI and EcoRV restriction enzymes. The 8.3 kb fragment which contained the A and B transposase genes was purified by gel electrophoresis and cloned in the circular vector pUC19 linearized with SmaI and EcoRI. The reconstituted plasmid was transformed in a suitable recipient bacterium. The colonies resistant to antibiotics were selected and were shown to contain the pPR30 plasmid (FIG. 2)

MC4100 (MudII1734) was transformed with pPR30 after treating the cells with calcium chloride (Mandel and Higa, J. Mol. Biol., 53, 159, 1970). After 2 hours at 30° C. in LB medium the cells were spread on dishes containing 20 μg/ml of Km, 25 μg/ml of ampicillin (Ap) and 10 μg/ml of X-gal. Incubation was carried out for 48 hours at 30° C. and colonies colored a blue of variable intensity appeared. These colonies were purified on the same medium and selected.

The total DNA was extracted from independent colonies, digested with EcoRI and then subjected to electrophoresis and transferred to a nylon membrane. After hybridization with the DNA of the radiolabeled transposon, several bands were detected on the autoradiogram indicating the amplification of the transposon. The pPR30 plasmid was eliminated from these strains by several successive transfers on LB medium without Ap.

The AM1 strain was studied in particular: after the DNA had been isolated, digested by EcoRI and subjected to electrophoresis, the DNA fragments were transferred to a nylon membrane. 4 hybridization bands can be seen in FIG. 3 (lane f) when the probe used is a radiolabeled pCE1134. These 4 hybridization bands correspond to two insertions of MudII1734.

Stability of the copy number of MudII1734 The strain AM1 : MC4100 (MudII1734) which has two copies of MudII1734 on its chromosome was cultured for 170 generations in LB liquid medium without Km. The copy number of MudII1734 on the chromosome was then measured by DNA—DNA hybridization (FIG. 3, lanes a to e). The copy number in this strain remained stable and no change in the restriction pattern could be detected, this indicating a high stability of the insertions.

Production of beta-galactosidase

The strain thus obtained is able to produce beta-galactosidase. The strains MC4100 (MudII1734) and AM1 produce, respectively, 7.10$^{-1}$ and 10 nMole/mn/mg of protein having a beta-galactosidase activity.

EXAMPLE 2

Production of L-Threonine by Amplification of the Genes Responsible for the Production of L-Threonine by Fermentation Construction of pCE1134

The strain POII1734 (Castilho et al., J. Bacteriol., 158, 488, 1984) was transformed with pCE100 (2.1 kb, Cm$^R$, FIG. 4) after treating the cells with calcium chloride (Mandel A. and Higa M., J. Vol. Biol., 53, (1970)).

The transformants were selected on dishes of LB medium containing 25 μg/ml of chloramphenicol (Cm) after 24 hours of incubation at 30° C. The transformant POII1734/pCE100 was cultured for 2 hours at 30° C. in 3 ml of LB medium, subsequently subjected to thermal shock for 15 minutes at 45° C. and then cultured at 37° C. for 2 hours, leading to a phage lysate. In order to obtain the phage solution, this lysate was mixed with several drops of chloroform and subsequently centrifuged. The supernatant was designated phage solution I.

*E. coli* M8820 (Mu) (Castilho et al., J. Bacteriol., 1, 488, 1984) was cultured overnight in an LB medium to which calcium chloride and magnesium sulfate were added to give a final concentration of 1 mM and 2.5 mM respectively. 200 μl of this culture and of phage solution I were mixed and left at room temperature for 15 minutes. After addition of 2 ml of LB medium and incubation at 30° C. for 2 hours, this cell suspension was spread on dishes of LB medium containing 20 μg/ml of Km and 25 μg/ml of Cm, and then incubated at 30° C. for 24 hours. The 20 clones which appeared on the dishes were harvested and plasmid extraction was carried out by the mini-preparation method (Birnboim and Doly, Nucleic Acids Res., 7, 1513, 1979). Analysis of the restriction map showed that all the clones exhibited a plasmid in which MudII1734 was inserted. One of them was designated pCE1134 (FIG. 4).

Construction of MidAN9 comprising the Thr operon pCE1134 was completely cleaved by the BamHI and then SalI restriction enzymes. The DNA fragment in which the lac operon is lacking was isolated by agarose gel electrophoresis and extracted from this gel.

The pAJ294 plasmid (Miwa et al., Agric. Biol. Chem., 47, 2329, 1983) was completely cleaved by the BamHI and then SalI restriction enzymes. After agarose gel electrophoresis, the DNA fragment containing the thr operon was extracted from the gel. The two DNA fragments were mixed and ligation was carried out at 10° C. for 16 hours using T4-DNA ligase, ATP and dithiothreitol. After transformation of the thrB mutant strain with the ligation mixture, the transformants were selected on a minimum medium containing 25 µg/ml of Cm and no threonine. The plasmid was extracted from one of the transformants and was found to contain Mud with the npt gene and the thr operon (pAM9, FIG. 5).

Transposition of MudAM9 on the chromosomal DNA

The *E. coli* strain JM109 (Yanisch-Perron et al., Gene, 33, 103–119 (1985)) (Mucts) was transformed with pAM9 after treatment with calcium chloride. The transformants were selected on dishes of LB medium containing 20 µg/ml of Km and 25 µg/ml of Cm, after incubation at 30° C. for 24 hours. The plasmids were extracted from 20 independent colonies and were found to be pAM9. JM109 (Mucts)/pAM9 was cultured at 30° C. for 2 hours after being subjected to thermal shock at 45° C. for 15 minutes. The culture was maintained at 37° C. for 2 hours. The culture was then mixed with a few drops of chloroform and left at room temperature for 15 minutes. The phage solution II was obtained at 10 minutes of centrifugation at 5,000 rpm.

To the culture of JM109 (Mucts) left overnight at 30° C. in LB medium there were added $CaCl_2$ and $MgSO_4$, giving a final concentration of 1 mM and 2.5 mM respectively. 200 µl of this solution and of phage solution II were mixed and left at room temperature for 15 minutes. After addition of 2 ml of LB medium, incubation was carried out at 30° C. for 2 hours, and this cell suspension was spread on dishes of LB medium containing 20 µg/ml of Km. After incubation at 30° C. for 24 hours, 100 colonies were harvested and their sensitivity to Cm was checked. 95% of them were sensitive to Cm and were confirmed as JM109 (Mucts) (MudAM9).

After culturing JM109 (Mucts) (MudAM9) at 30° C. for 2 hours in LB medium, thermal shock treatment was carried out for 15 minutes at 45° C. followed by incubation at 37° C. for 2 hours. A few drops of chloroform were then added and centrifugation was carried out at 5,000 rpm for 10 minutes. The supernatant obtained was phage solution III.

To the *E. coli* strain AJ11332 (Shiio et al., Agric. Biol. Chem., 33, 1152, 1969), cultured overnight, there were added $CaCl_2$ and $MgSO_4$, giving final concentrations of 1 mM and 2.5 mM respectively. 200 µl of this solution and the phage solution III were mixed and left at room temperature for 15 minutes. After addition of 2 ml of LB medium, incubation was continued at 30° C. for 2 hours. The cell suspension was spread on dishes of LB medium containing 20 µg/ml of Km and then incubated at 30° C. for 24 hours. 100 colonies were harvested and tested for their lysis at 45° C. and their sensitivity to the Mu phage. One of these strains was designated EL1001.

Amplification of MadAM9 on the chromosomal DNA and choice of the copy number (i) Amplification of MudAM9 by pPR30:
Strain EL1001 was transformed with pPR30. The transformants were selected on dishes of LB medium containing 25 µg/ml of Ap and a variable quantity of Km and/or of neomycin (Nm).

(ii) Amplification by lysate of Mucts:
Strain EL1001 was infected by a lysate of Mucts, such as described hereinabove, and then spread on dishes of LB medium containing variable quantities of Km.

The clones obtained from pPR30 in the case of (i) and those obtained from Mu in the case of (ii) were selected in order to provide a stable number of copies of MudAM9.

After incubation at 30° C. for 48 hours, the colonies were harvested and the number of MudAM9 on the chromosomal DNA was measured by the hybridization method described hereinabove.

Strains EL1002 and EL1003 will be studied more particularly.

The DNA was extracted from strains AJ11332, EL1001, EL1002 and EL1003. After digestion by the EcoRI restriction enzyme, the DNA was subjected to electrophoresis and transferred to a nylon membrane. The DNA was then hybridized with small radiolabeled pAM9 fragments digested by EcoRI. The results are shown in FIG. 6. Bands A, B, C and D correspond respectively to the strains AJ11332, EL1001, EL1002 and EL1003. The letter a corresponds to the wild type of the thr operon, and the letter b corresponds to an unidentified band seen in lanes B, C and D. The numbers correspond to MudAM9-specific bands. According to these results -strains EL1001, EL1002 and EL1003 have 1, 4 and 10 copies (at least) of MudAM9.

The relationship between the copy number of MudAM9 in the strain and the concentration of antibiotics to which the strain is resistant is summarized in Table I:

TABLE I

Relationship between the copy number of MudAM9 and antibiotic resistance

| No. of copies of MudAM9 | Resistance | Sensitivity |
| --- | --- | --- |
| 0 | | 20 µg/ml KM |
| 1 | 200 µg/ml Km | 250 µg/ml of Km and Nm |
| 2 (or more) | 250 µg/ml of Km and Nm | |

Production of L-threonine

The strains having amplified MudAM9 were refreshed on dishes of LB medium at 30° C. for 24 hours and inoculated in 20 ml of the production medium described hereinbelow.

Composition of the production medium

Glucose: 30 g/l, $(NH_4)_2SO_4$: 10 g/l, $KH_2PO_4$: 1 g/l, $MgSO_4 7H_2O$: 1 g/l, $FeSO_4\ 7H_2O$: 10 mg/l, MnSO, 4–6$H_2O$: 10 mg/l, L-Met: 0.1 g/l, L-Ile: 0.1 g/l, L-Pro: 0.45 g/l, RNA: 2 g/l, thiamine HCl: 1 mg/l and $CaCO_3$: 40 g/l (pH: 7.0).

The culture was stirred at 30° C. for 72 hours. The quantity of threonine in the medium was measured with an amino acid analyzer. The results are shown in Table II:

TABLE II

Production of L-threonine by strains containing MudAM9

| Strain | Estimation of the copy number of MudAM9 | L-Thr (g/l) |
| --- | --- | --- |
| AJ11332 | 0 | 3 |
| EL1001 | 1 (at least) | 3.3 |
| EL1002 | 4 (at least) | 8.9 |
| EL1003 | 10 (at least) | 12 |

Stability and L-threonine productivity

Strain EL1002 containing 4 copies of MudAM9 was transferred on several successive occasions onto dishes of LB medium without antibiotics, and after each transfer the L-threonine productivity was tested by using the method described given above. The results are shown in Table III:

TABLE III

Stability of L-threonine production after repeated transfers on LB media without antibiotics with strain EL1002

| Number of transfers | 0 | 2 | 4 | 6 | 8 | 10 |
|---|---|---|---|---|---|---|
| L-Thr production | 8.5 | 8.6 | 8.5 | 8.8 | 8.8 | 8.9 |

Table IV shows the specific activities of the L-Thr biosynthesis enzymes of strains containing MudAM9:

TABLE IV

High-quantity production of L-threonine biosynthesis enzymes by AJ11332 (mudAM9)

| Strain | Specific activities (*) | |
|---|---|---|
| | AK1 | HDHI |
| AJ11332 | 2.5 | 4.8 |
| EL1001 | 4.0 | 10.1 |
| EL1002 | 12.5 | 25.0 |
| EL1003 | 22.5 | 37.4 |

(*) The specific activities are given in $\mu$mole/min/mg of protein

EXAMPLE 3
Amplification of MUD with a PLASXID Containing Thermoinductible Transposases Construction of a plasmid containing thermoinductible transposases The strain POII1681 : M8820 (Mucts) (MudII1681) (Castilho et al., J., Bacteriol., 158, 488 (1984)) was transformed, after treating the bacteria with $CaCl_2$ (Mandel M. and Higa A., J. Mol. Biol., 53, 159 (1970)), with the pEVl1 plasmid (FIG. 7). After 24 hours of incubation at 30° C. the transformants were selected on dishes of LB medium containing 20 $\mu$g/ml of Ap and 20 $\mu$g/ml of Km. A transformant POII1681/pEV11 was cultured for 2 hours at 30° C. in 3 ml of LB. The culture was then subjected to thermal shock for 15 minutes at 45° C. followed by culturing at 37° C. for 2 hours. A few drops of chloroform were added, and after centrifugation at 5,000 rpm for 10 minutes the phage solution was obtained. The strain E. coli: M8820 (Mu) (Castilho et al., J., Bacteriol., 158, 488 (1984)) was cultured overnight in LB medium; $CaCl_2$ and MgSO. were added, giving final concentrations of 1 mM and 2.5 mM respectively. To 200 $\mu$l of this culture 50 $\mu$l of the phage solution were added, this suspension being left at room temperature for 15 minutes.

After adding 2 ml of LB and stirring for 2 hours at 30° C., the suspension of bacteria was spread on dishes of LB medium containing 20 $\mu$g/ml of Ap and 20 $\mu$g/ml of Km; incubation was carried out for 24 hours at 30°C. 20 colonies were obtained and their plasmid DNAs were extracted by the mini-preparation method (Birnboim and Doly, Nucleic Acid Res. 7, 151.3 (1979)). After analyses of the restriction map, the clones were found to contain an insertion of the MudII1681 in the pEV11 plasmid. One of the plasmids is designated pMC1 (FIG. 7).

The pMC1 plasmid was digested by the BamHI and BalII restriction enzymes and then ligated with pRC100 (see Example 2) cut by BamHI. The strain MC1060 was transformed by the ligation mixture. The transformants were selected on dishes of LB medium containing 25 $\mu$g/ml of Cm and 20 $\mu$g/ml of Ap. The plasmids of 30 transformants were extracted and analyzed; one of them was designated pMC23 (FIG. 7).

Amplification of the defective MudAM9 phage with the pMC23 plasaid

The strain EL1001 containing the defective MudAM9 phage (see Example 2) was transformed, after treatment with $CaCl_2$ (Example 2), by the pMC23 plasmid. The transformants were selected on dishes of LB medium containing 20 $\mu$g/ml of Ap and 25 $\mu$g/ml of Cm after an incubation of 24 hours at 30° C.

A transformant EL1001/pMC23 was cultured in LB medium containing 20 $\mu$g/ml of Ap and 25 $\mu$g/ml of Cm for 2 hours at 30° C. 1 ml of this culture was subjected to a thermal shock for 15 minutes at 45° C., then 1 ml of LB was added; the incubation took place at 30° C. for 2 hours.

This bacterial suspension was spread on dishes of LB medium containing 400 $\mu$g/ml of Nm and Km; incubation was carried out at 30° C. for 48 hours. 50 clones appeared and were tested for their sensitivity to Cm and their L-Thr production (Example 2). 50% of them were Cm-sensitive and 60% produced more L-threonine than the host strain.

Several clones were thus selected, and their copy number of MudAM9 was measured by the DNA—DNA hybridization technique (Southern, 1975, J. Mol. Biol., 98, 503). The chromosomal DNAs were digested by the HindIII restriction enzyme. After electrophoresis, the DNAs were absorbed on a nylon membrane and then hybridized with the SalI-BamHI fragment (labeled by sulfonation), containing the threonine operon, of the pAK9 plasmid as the probe.

Figure 8A:
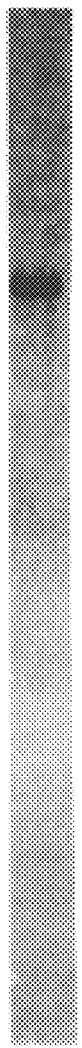
FIGS. 8A–8C: represents the analyses of the transpositions of MudAM9 by the Southern DNA—DNA hybridization technique in strains AJ11332, EL1008 and EL1009.
Figure 8B:
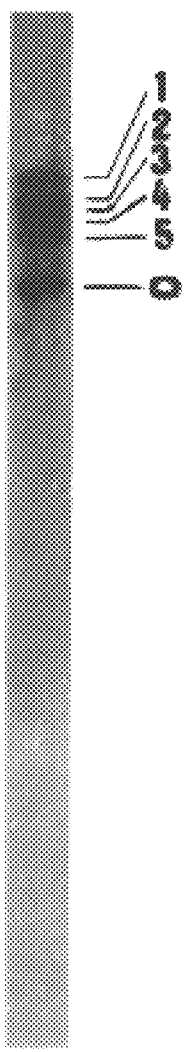
Figure 8C:
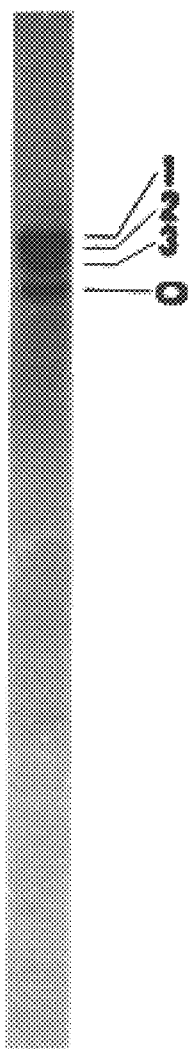

The results relating 'to the production of L-threonine and the copy number of MudM are given in Table V and FIG. 8. Lanes A, B and C correspond respectively to the strains AJ11332, EL1008 and EL1009.

In the A lane the "o" band corresponding to the threonine operon is shown. In lane B at least 6 bands are shown: band "o" and 5 bands which are numbered 1 to 5 and which correspond to 5 copies (at least) of MudAM9. In lane C, in addition to the "o" band, 3 bands are shown numbered 1 to 3 and corresponding to 3 copies at least of MudAM9.

TABLE V

Copy number of MudAM9 and production of L-threonine in strains EL1008 and EL1009

| Strain | Copy number | L-Thr (g/l) |
|---|---|---|
| EL1008 | 5 | 7 |
| EL1009 | 3 | 5 |

EXAMPLE 4
Amplification of Two Different Defective Phages on the Chromosomal DNA of a Strain Preparation of a lysate containing NudIIPR13 After culturing the strain MC4100 (Mucts) (MudII-PR13) (P. Ratet et al., Gene, 63, 41–52, 1988) in LB medium for 2 hours at 30° C., a thermal shock was carried out for 15 min at 45° C., followed by incubation at 37° C. for 2 hours. A few drops of chloroform were added, and then centrifugation was carried out at 5,000 rpm for 10 minutes. The phage lysate VI was thus obtained.

Transposition of MudIIPR13 on the chromosomal DNA
To an overnight culture of strain EL1001, $CaCl_2$ and MgSO. were added, giving final concentrations of 1 mM and 2.5 mM respectively. 50 $\mu$l of the phage solution VI were added to 200 $\mu$l of the EL1001 culture, and the suspension was then left to stand at room temperature for 15 min. After addition of 2 ml of LB, the suspension was stirred at 30° C. for 2 hours. The bacteria were then spread on an LB medium containing 25 $\mu$g/ml of Cm and 20 $\mu$g/ml of Km. After incubation for 24 hours at 30° C., 50 colonies were subcultured and then tested for their lysis at 45° C. and for their sensitivity to the Mu phage. 80% of the colonies tested were sensitive to Mu and did not lyse at 45° C. One EL1001 (MudIIPR13) strain was designated EL1004.

The strain EL1003 was treated in the same manner.

One EL1003 (MudIIPR13) strain was designated EL1005.

Amplification of MudIIPR13 in the EL1004 and EL1005 strains

The EL1004 strain was infected by a Mucts lysate prepared from the JM109 (Mucts) strain by the method described in Example 2. The bacterial suspension was spread on dishes of LB medium containing 20 µg/ml of Km and 400 µg/ml of Cm. After incubation for 48 hours at 30° C., 50 colonies were isolated and then tested for their lysis at 45° C. and for their sensitivity to the Mu phage. 84% of the clones were sensitive to Mu and did not lyse at 45° C. One of these clones was designated EL1006.

The EL1005 strain was treated in the same manner and the EL1007 clone was obtained.

The chromosomal DNAs were extracted from strains AJ11332, EL1001, EL1003, EL1004, EL1005, EL1006 and EL1007.

Figures 9A, 9B, 9C, 9D, 9E, 9F, 9G:
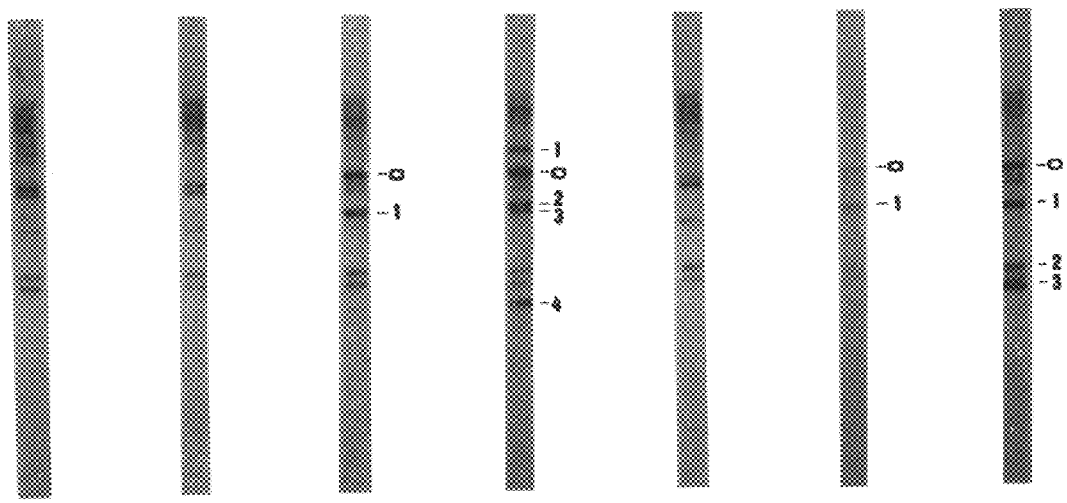
FIGS. 9A–9G: shows the results of the electrophoresis followed by blot hybridization of the DNA of strains AJ11332, EL1001, EL1004, EL1006, EL1003, EL1005 and EL1007 respectively for lanes A to G (the probe corresponds to the pRC100 plasmid digested by HindIII).

After digestion of the chromosomal DNAs by the EcoRI restriction enzyme, a DNA—DNA hybridization was carried out by the Southern method (Example 3). The probe corresponded to the pRC100 plasmid digested by HindIII and labeled by sulfonation. In FIG. 9 the lanes A, B, C, D, E, F and G correspond respectively to strains AJ11332, EL1001, EL1004, EL1006, EL1003, EL1005 and EL1007.

The bands obtained in the lanes A, B and E correspond to the hybridization between the pRC100 probe and the chromosomal DNAs of the strains. These bands are present in all the other lanes and are not therefore specific to MudIIPR13. In lanes C, D, F and G the numbers 1 to 4 mark the bands having a specificity for hybridization with MudIIPR13, each band corresponding to an insertion of the MudIIPR13. In these same lanes the "o" band corresponds to an internal band of the MudIIPR-13. According to these results strains EL1004 and EL1005 contain 1 insertion of the MudIIPR13; strains EL1006 and EL1007 contain, respectively, 4 and 3 insertions of MudIIPRI3 at least.

EXAMPLE 5
Integration and Amplification of Defective Phages in an Erwinia chrysantsrmi Strain Preparation of lysates of MudII1734 and MudAM9

Two phage lysates containing MudII1734 and MudAM9 were prepared from strains: POII1734 (Castilho et al., J. Bacteriol., 158, 488 (1984)) and JM109 (Mucts) (MudAM9) (Example 2) according to the method described in Example 2.

Transposition of the Mud phages on the chromosomal DNA of Erwinia chrysanthemi

The E. chrysanthemi strain 384551 (M. Chippaux, CNRS, Marseilles) was used as the recipient strain. The transduction (Example 2) was carried out using 2 lysates (Example 2). The colonies capable of growing in a medium containing 20 µg/ml of Km were isolated and then tested for their lysis at 45° C. and their sensitivity to the Mu phage. 70% and 80% respectively of the transductants obtained after infection by the MudII1734 and MudAM9 lysates were sensitive to the Mu phage and did not lyse at 45° C. One clone from each transduction was selected:
EL3003: E. chrvsanthemi (MudII1734)
EL3004: E. chrysanthemi (MudAM9)

The amplification of the Mud phages in strains EL3003 and EL3004 was carried out using a lysate of strain JM109 (Mucts) as described in Example 2. The selection of the strains containing the amplified Mud was effected in an LB medium containing 400 µg/ml of Km and Nm.

50 resistant colonies were subcultured and then tested for their Mu phage-sensitivity. Strains EL3007 and EL3008 sensitive to the Mu phage were thus obtained.

Copy number of Mud on the chromosomal DNA of the two strains

The chromosomal DNA was extracted by the same, technique as for E. coli (Example 1) except for a treatment with SDS in place of sarcosyl. Molecular analysis of these DNAs was carried out by the Southern method (Example 3). The -NAs were digested by the EcoRI restriction enzyme. The probes used were specific to the defective phages and were labeled by sulfonation:
For MudII1734: EcoRI-HindIII fragment of the pAM9 plasmid corresponding to the left border of the defective phage.
For MudAM9: SalI-BamHI fragment of the pAM9 plasmid corresponding to the threonine operon of E. coli.

Figure 10A:
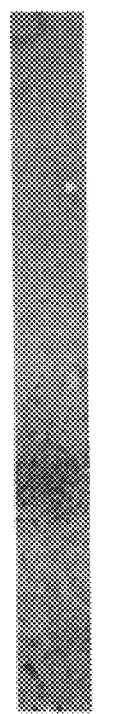
FIGS. 10A–10C: shows the results of electrophoresis followed by blot hybridization of the DNA of strains E. chrysanthemi 384551, EL3003 and EL3007 for lanes A, B and C respectively (the probe used is the EcoRI-HindIII fragment of pAM9 plasmid).
Figure 10B:
Figure 10C:
Figures 11A, 11B, 11C:
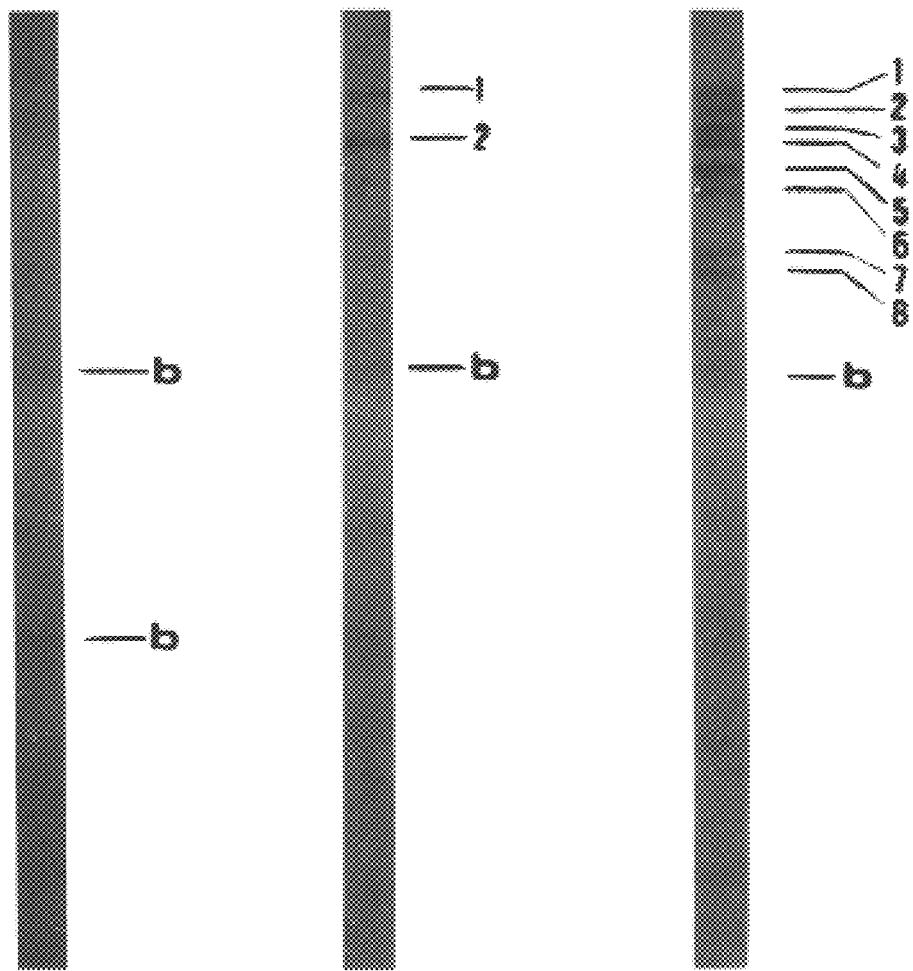
FIGS. 11A–11C: shows the results of electrophoresis followed by blot hybridization of the DNA of strains *E. chrysanthemi* 384551, EL3004 and EL3008 for lanes A to C respectively (the probe used is the Sal-BamHI fragment of the pAM9 plasmid.

The results are shown in Table VI and FIGS. 10 and 11.

In FIG. 10 the lanes A, B and C correspond respectively to the strainst E. chrysanthemi 384551, EL3003 and EL3007.

In lanes B and C, 1 and 3 bands appear corresponding to a hybridization specificity with MudII1734. According to these results strains EL3003 and EL3007 possess, respectively, 1 and 3 insertions (at least) of MudII1734.

In FIG. 11 lanes A, B and C correspond respectively to the strains: E. chrysanthemi 384551, EL3004 and EL3008.

In lane A the "b" fragment corresponds to a hybridization between the probe and the chromosomal DNA of the 384551 strain. This fragment is also found in all the other lanes.

In lanes B and C the numbers correspond to bands having a specificity of hybridization with MudAM9. Two bands correspond to one insertion of MudAM9.

According to these results strains EL3004 and EL3008 possess, respectively, 1 and 4 insertions at least of MudAM9.

TABLE IV

Copy number of Mud in strains of E. chrysanthemi

| Strain | Copy number |
| --- | --- |
| EL3003 | 1 |
| EL3004 | 1 |
| EL3007 | 3 (at least) |
| EL3008 | 4 (at least) |

EXAMPLE 6
Amplification of a Defective Phage of Larger Size

Construction of the MudAM11 comprising the threonine operon and the asd gene

The pAM9 plasmid (see Example 2), containing the defective MudAM9 phage, is completely cleaved by the BamHI restriction enzyme (single site); pAM9 is thus linearized.

The pAD20 plasmid (Haziza et al., EMBO, J., 1982, 3, 379–384) is completely cleaved by the BamHI restriction enzyme. After electrophoresis, the fragment containing the asd gene is extracted from the gel.

The two DNA fragments are mixed and ligation is carried out at 22° C. for 1 hour, using T4-DNA ligase, ATP and dithiothreitol. After transformation of a mutant strain Asd⁻: JCP203 (C. PRINTZ, personal communication) with the ligation mixture, the transformants were selected in a complete medium containing 25 μg/ml of Cm and 20 μg/ml of Km. A plasmid extracted from the transformants was found to have the defective MudAM11 phage containing the nptII gene, the threonine operon and the asd gene. This plasmid designated pAM11 is shown in FIG. 12.

Transposition of MudAM11 on the chromosomal DNAs

The strain JM109 (Mucts)/pAM11 was obtained by transformation of the strain of E. coli JM109 (Mucts) (see Example 2, page 14, lines 5 to 11), by the pAM11 plasmid.

The strain JM109 (Mucts)/pAM11 was cultured at 30° C. for 2 hours. After being subjected to thermal shock at 45° C. for 15 minutes, the cultures were maintained at 37° C. for 2 hours. A few drops of chloroform were then added to this culture and it was left at room temperature for 15 minutes. The phage solution II-AM11 was obtained after 10 minutes of centrifugation at 5,000 rpm.

To the culture of JM109 (Mucts) left overnight at 30° C. in LB medium there were added $CaCl_2$ and MgSO4 giving final concentrations of 1 mM and 2.5 mM, respectively. 50 μl of the phage solution II-AM11 were mixed with 200 μl of this culture and left at room temperature for 15 minutes. After addition of 2 ml of LB medium, the mixture was stirred for 2 hours at 30° C. and the bacterial suspension was then spread on dishes of LB medium containing 20 μg/ml of Km. After incubation at 30° C. for 24 hours, 100 colonies were harvested and tested for their sensitivity to Cm, 85% of them showing such sensitivity, and one clone being designated JM109 (Mucts) (MudAM11).

After culturing strain JM109 (Mucts) (MudAM11) for 2 hours at 30° C. in LB medium, a thermal shock treatment was carried out for 15 minutes at 45° C. After incubation for 2 hours at 37° C., a few drops of chloroform were added and centrifugation was carried out at 5,000 rpm for 10 minutes.

The supernatant obtained was the phage solution III-AM11.

The strain AJ11332 ($\lambda^+$, $Pro^-$) was transduced by a P1 phage cultured in a $Pro^+$ strain. A strain AJ11332 ($\lambda^+$, $Pro^+$) was selected. The λ phage contained in this strain was then eliminated (C. MOREL, personal communication). The strain thus obtained: AJ11332 ($\lambda^-$, $Pro^+$) was designated EL1016. To the strain of E. coli EL1016, cultured overnight at 37° C. in LB, there were added $CaCl_2$ and $MgSO_4$, giving final concentrations of 1 mM and 2.5 mM respectively. 50 μl of the phage solution III-AM11 were mixed with 200 μl of this culture and left at room temperature for 15 minutes. After addition of 2 ml of LB, stirring was carried out for 2 hours at 30° C. The bacterial suspension was spread on dishes of LB medium containing 20 μg/ml of Km, then incubation was carried out for 24 hours at 30° C. A Mu-sensitive clone was selected: EL1012.

Amplification of MudAM11 on chromosomal DNAs and choice of copy number

The amplification was effected by infection of the EL1012 strain by a Mucts phage lysate obtained as above. The bacteria were spread on dishes of LB medium containing variable quantities of Km and Nm ranging from 250 to 1200 μg/ml.

The selected transductants contained a stable number of copies of MudAM11.

The strain EL1013 was studied more particularly.

The MudAM11 number on the chromosomal DNAs was evaluated by the Southern DNA—DNA hybridization method described in Example 3.

The chromosomal DNAs were extracted from strains EL1016, EL1012 and EL1013 respectively. After digestion by the SalI or EcoRI restriction enzymes, these DNAs were subjected to electrophoresis and were then absorbed on a nylon membrane (see Example 3). They were then hybridized with a DNA fragment labeled (by sulfonation) as the probe (FIGS. 13, 14, 15 and 16), lanes A, B and C corresponding respectively to strains EL1016, EL1012 and EL1013.

The letter "a" corresponds to the wild type of the threonine operon or the asd gene. The letter "p" corresponds to partial digestions of the DNAs. The numbers correspond to the bands marking a specificity of hybridization with MudAM11.

Figure 13A:
In FIGS. 13A–13C the chromosomal DNAs are digested by SalI and are hybridized with the EcoRI-HindIII fragment containing the genes nttII, thrA, thrB and thrC' of pAM9 as the probe.
Figure 13B:
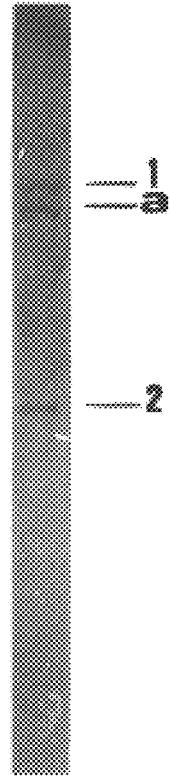
Figure 13C:
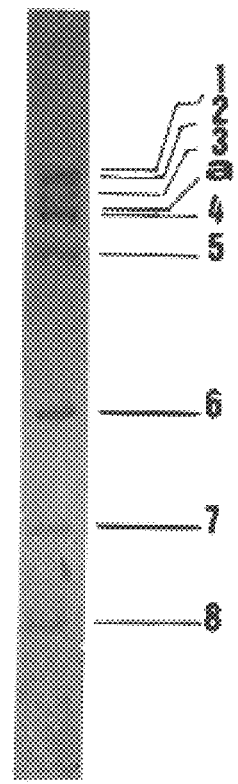

In FIG. 13 the chromosomal DNAs were digested by SalI and hybridized with the EcoRI-HindIII fragment containing the nMtII, thrA, thrB and thrC' genes, of pAM9 as the probe.

Two bands correspond in this case to one insertion of MudAM11.

In lane A only the "a" band corresponding to the original threonine operon is shown.

In lane B three bands are shown: "a" and "1" and "2" which correspond to an insertion of MudAM11.

In lane C nine bands are shown: "a" and "i" to "8" which correspond to 4 insertions (at least) of MudAM11.

Figure 14A:
In FIGS. 14A–14C the chromosomal DNAs are digested by EcoRI and hybridized with the EcoRI-HindIII fragment containing the genes nptII, thrA, thrB and thrC' of pAM9 as probe.
Figure 14B:
Figure 14C:

In FIG. 14 the chromosomal DNAs were digested by EcoRI and hybridized with the EcoRI-HindIII fragment containing the nptII, thra, thrB and thrC' genes of pAM9 as the probe. One band corresponds to one insertion of MudAM11.

In lane A only the "a" band corresponding to the threonine operon is shown.

The "p" band corresponds to a partial digestion. In lane B two bands are shown: "a" and "1" corresponding to an insertion of MudAM11.

The "p" band corresponds to a partial digestion.

In lane C six bands are shown: "a" and "1" to "5" corresponding to 5 insertions (at least) of MudAM11.

In FIG. 15 the chromosomal DNAs were digested by SalI and hybridized with the BamHI fragment, containing the asd gene, of pAM11 as the probe.

One band thus corresponds to one insertion of MudAM11.

In lane A only the "a" band is shown, corresponding to the asd gene.

In lane B two bands are showns "a" and "1", that is one insertion of MudAM11.

In lane C five bands are shown: "a" and "1" to "4" which correspond to 4 insertions (at least) of MudAM11.

In FIG. 16 the chromosomal DNAs were digested by EcoRI and hybridized with the BamHI fragment, containing the asd gene, of pAM11 as the probe.

One band corresponds to one insertion of MudAM11.

In lane A only'the "a" band corresponding to the asd gene is shown.

In lane B two bands are shown: "a" and "1", that is one insertion of MudAM11.

In lane C six bands are shown: "a" and "1" to "5", that is 5 insertions (at least) of MudAM11.

According to these results strains EL1012 and EL1013 are, respectively, one and five copies (at least) of MudAM11.

TABLE VII

Relationship between the copy number of MudAM11 in the strains and the antibiotic concentrations to which they are resistant

| Copy number MudAM11 | Resistance | Sensitivity |
|---|---|---|
| 0 | | 20 μg/ml Km |

TABLE VII-continued

Relationship between the copy number of MudAM11
in the strains and the antibiotic concentrations
to which they are resistant

| Copy number MudAM11 | Resistance | Sensitivity |
|---|---|---|
| 1 | 200 μg/ml Nm and Km | 250 μg/ml Nm and Km |
| 5 (or more) | 250 μg/ml Nm and Km | 1200 μg/ml Nm and Km |

TABLE VIII

Production of L-threonine by strains EL1012
and EL1013 containing the defective MudAM11 phage
The strains having amplified MudAM11 were sub-
cultured in dishes of LB medium at 30° C. for 24 hours and
inoculated in 20 ml of the production medium (Example 2).
Culturing was carried out at 30° C. for 72 hours. The
quantity of L-threonine, in the medium was measured using
an amino acid analyzer.

| Strains | Estimation of the copy number of MudAM11 | L-Thr (g/l) |
|---|---|---|
| EL1016 | 0 | 3.0 |
| EL1012 | 1 | 5.3 |
| EL1013 | 5 (at least) | 10.2 |

TABLE IX

Specific activities of the L-threonine biosynthesis
enzymes of the strains containing MudAM11
The aspartokinase-I (AK-I) activity was assayed
by the method of Truffa-Bachi, P., Cohen, G-N., Methods
Enzymology, 1970, 17, 694–702.
The aspartate semialdehyde dehydrogenase (ASA)
activity was measured using the technique of Hegeman, G-
D., Cohen, G-N., Margan, R., Methods Enzymology, 1970,
17, 708–713.

| | Specific activities μ/mole/min/mg a of proteins | |
|---|---|---|
| Strains | AK-1 | ASA |
| EL1016 | 4.9 | 0.32 |
| EL1012 | 4.0 | 0.54 |
| EL1013 | 21.1 | 1.14 |

EXAMPLE 7

Amplification of the aspA Gene of *E. coli* with a View to the Production of L-Aspartate Ammonia-Lyase Construction of MadAB9 comprising the asUA gene coding for the L-aspartate amonia-lyase of *E. coli*

The pGS94 plasmid (Guest et al., J. Gen. Microbiol. (1984), 130, 1271–1278) containing the aspA gene is completely cleaved by the ClaI and SalI restriction e enzymes. The 3.4 Kb fragment contains the aspA gene.

The pPC3 glasmid (resulting from inversion of PstI fragment of pPR3 plasmid ; GENE, Vol. 42, (1986) pages 185–192) containing the defective MudPC3 phage is completely cleaved by the ClaI and SalI restriction enzymes. The 5.3 Kb fragment contains the defective phage in which it is desired to clone the aspA gene.

The two cleaved plasmids are mixed and ligation is carried out at 22° C. for 1 hour, using T4-DNA ligase, ATP and dithiothreitol. After transformation (Example 2) of the MC1060 strain with the ligation mixture, the transformants are selected on LB medium containing 20 μg/ml of Ap and 25 μg/ml of Cm.

27 transformants were subcultured on LB medium containing 20 μg/ml of Km; 17 clones sensitive to this antibiotic were retained.

The L-aspartate ammonia-lyase activity was assayed using acellular extracts of cultures of these clones according to the method of Spencer et al., J. Gen. Microbiol. (1976), 97, 73–82. Only clone 9 had an AspA activity higher than the activity conferred by the chromosomal gene of the MC1060 strain.

Figure 17:
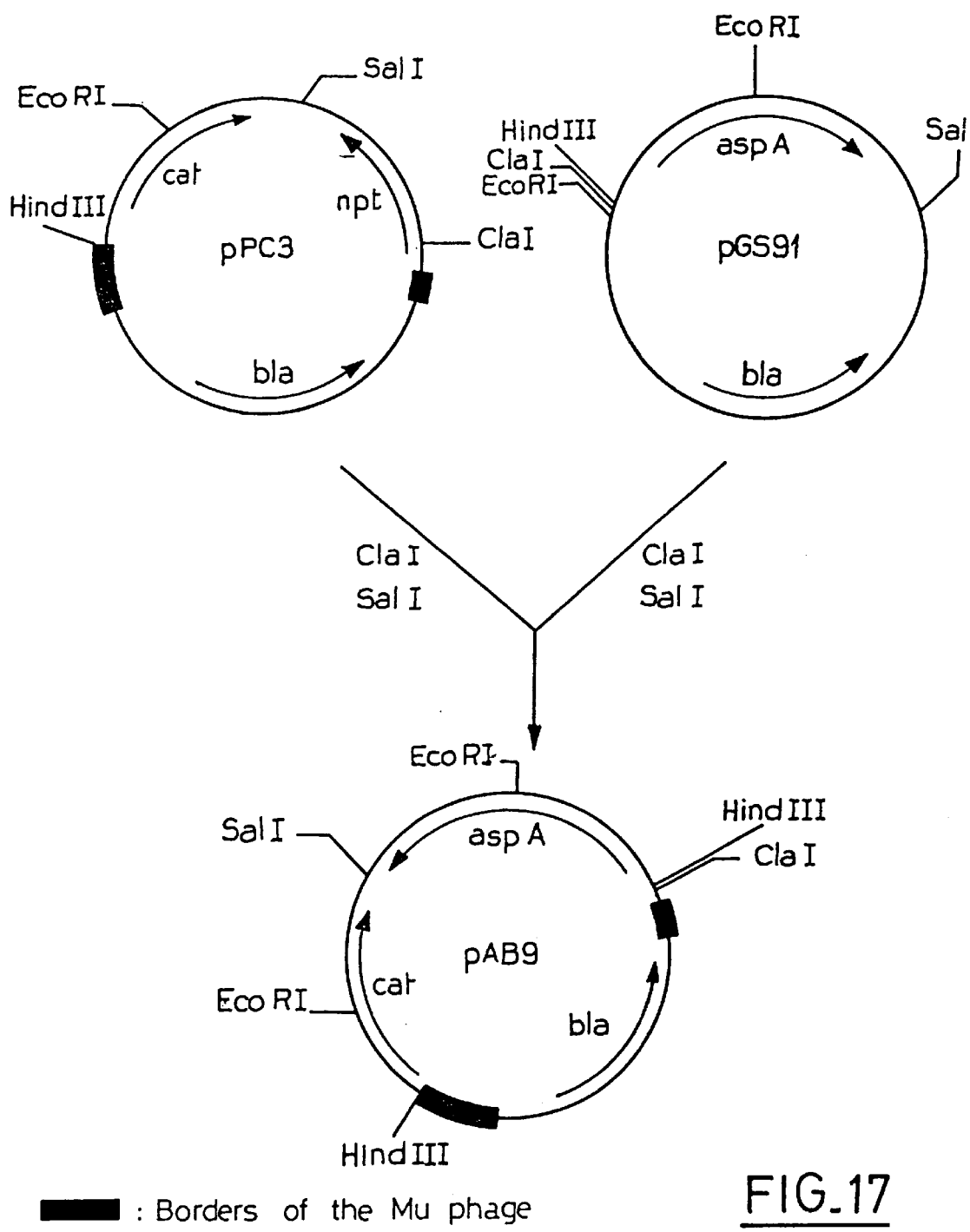
FIG. 17: represents the cloning of the aspA gene in a defective phage.

The plasmid DNA of this clone was extracted using the Birboim and Doly technique and then cleaved by the EcoRI and HindIII restriction enzymes. In parallel, the DNAs of the two parent plasmids were cleaved by the same restriction enzymes. Analysis of the restriction profiles showed that clone 9 corresponds to the cloning of the fragment containing the aspA gene in the defective MudPC3 phage. The new defective phage was designated MudAB9 and the plasmid carrying it pAB9 (FIG. 17).

Transposition of MudAB9 on chromosomal DNAs

The strain JM109 (Mucts)/pAB9 was obtained by transformation of the strain *E. coli* JM109 (Mucts) (Example 2) by plasmid pAB9.

The strain JM109 (Mucts)/pAB9 was cultured at 30° C. for 2 hours. After being subjected to thermal shock at 45° C. for 15 minutes, the culture was maintained at 37° C. for 2 hours. A few drops of chloroform were then added; after centrifugation at 5,000 rpm for 10 minutes, the phage lysate II-AB9 was thus obtained.

The strain JM109 (Mucts) was cultured overnight at 30° C. in LB medium. $CaCl_2$ and MgSO4 were then added, giving concentrations of 1 mM and 2.5 mM respectively. To 200 μl of this culture 50 μl of phage lysate II-AB9 were added. After 15 minutes of adsorption at room temperature, 2 ml of LB were added and the tubes were stirred at 30° C. for 2 hours. The suspension was then spread on dishes of LB medium containing 25 μg/ml of Cm.

The dishes were placed in an oven at 30° C. for 24 hours. 100 colonies were picked up and checked for their sensitivity to ampicillin. Strain JM109 (Mucts) (MudAB9) was thus obtained. The phage lysate III-AB9 was obtained from this strain as previously described.

To the strain *E. coli* MC41000, cultured overnight at 37° C. in LB medium, $CaCl_2$ and $MgSO_4$ were added to give concentrations of 1 mM and 2.5 mM respectively. The phage solution III-AB9 was mixed with 200 μl of this culture and left at room temperature for 15 minutes. After addition of 2 ml of LB, incubation was continued at 30° C. for 2 hours. The cell suspension was spread on a dish of LB medium containing 25 μg/ml of Cm. The dish was then placed in an oven at 30° C. for 24 hours. An Mu-sensitive clone was selected: EL1010.

Amplification of MudAB9 on chromosomal DNAs Determination of copy-number

Amplification was carried out by infection of the EL1010 strain by a Mucts lysate obtained as described hereinabove. The bacteria were spread on dishes of LB medium containing 500 μg/ml of Cm.

The selected transductants contained a stable copy number of MudAB9.

After incubation at 30° C. for 48 hours, the resistant colonies were picked up and the copy number of defective MudAB9 phages was determined by the Southern DNA-hybridization method (Example 3).

Strains EL1010 and EL1011 were studied in particular.

The DNA was extracted from strains MC4100, EL1010 and EL1011. After digestion by the SalI restriction enzyme, the DNA was subjected to electrophoresis and then absorbed on a nylon membrane. The DNA was subsequently hybridized with a plasmid labeled by sulfonation containing the asDA gene.

Figure 18A:
FIGS. 18A–18C: shows the results of electrophoresis followed by blot hybridization of the DNA of strains MC4100, EL1010 and EL1011 for lanes A to C respectively.
The probe is a plasmid containing the asUA gene (the DNA was digested by SalI).
Figure 18B:
Figure 18C:

In FIG. 18 lanes A, B and C correspond respectively to strains MC4100, EL1010 and EL1011.

The letter "a" corresponds to the wild type of the aspA gene.

In lane A, only the "a" band corresponding to the aspA gene is shown.

In lane B two bands are shown: "a" corresponding to the aspA gene, and "1" corresponding to an insertion of MudAB9.

In lane C five bands (at least) are shown: the "a" band and the "1" to "4" bands corresponding to 4 insertions (at least) of MudAB9.

TABLE X

Relationship between the copy number of MudAB9 in the strains, and their specific L-aspartate ammonia-lyase activity

| Strains | Copy number of MudAB9 | Specific activity Δ DO/mn/mg Prot. |
|---|---|---|
| MC4100 | 0 | 0.33 |
| EL1010 | 1 | 0.60 |
| EL1011 | 4 (at least) | 2.04 |

EXAMPLE 8

Several Insertions in One Lysogenization Stage

A phage lysate was obtained from strain JM109 (Mucts) (MudAM9) as described in Example 2.

To an overnight culture of the strain E. coli: EL 1016 (Example 6), $CaCl_2$ and $MgSO_4$ were added to give final concentrations of 1 mM and 2.5 mM respectively. To 200 µl of this culture 50 µl of phage solution III-AM9 were added (Example 2) and this suspension was left at room temperature for 15 minutes.

After addition of 2 ml of LB, incubation was carried out for 2 hours at 30° C. The bacterial suspension was spread on dishes of LB medium containing 250 µg/ml of Km and Nm; incubation was carried out for 24 hours at 30° C. Two colonies appeared and were tested for their lysis at 45° C., and for their sensitivity to the Mu phage. These two clones did not lyse, were sensitive to Mu and were designated EL1014 and EL1015.

An L-threonine production test was carried out as described in Example 2. The copy number of MudAM9 was measured by the Southern DNA—DNA hybridization method (Example 3). The chromosomal DNAs were digested by the HindIII restriction enzyme. After electrophoresis, the DNAs were absorbed by a nylon membrane and then hybridized with the SalI-BamHI fragment (labeled by sulfonation), containing the threonine operon, of the pAM9 plasmid. The results concerning L-threonine production and the copy number of MudAM9 are given in Table XI and FIG. 19.

Figures 19A, 19B, 19C:
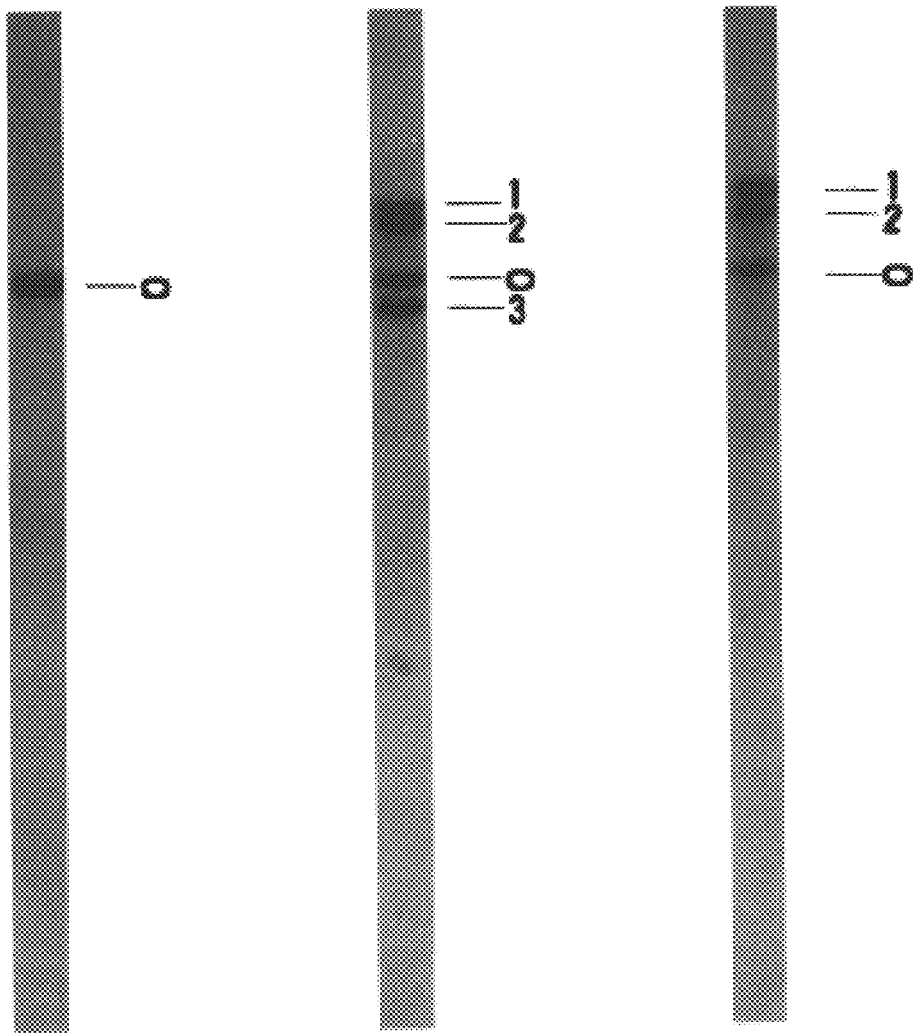
FIGS. 19A–19C: shows the results of electrophoresis followed by blot hybridization of the DNA of strains EL1016, EL1014, EL1015 for lanes A to C respectively.
The probe is the SalI-BamHI fragment containing the threonine operon of the pAM9 plasmid, the DNA is digested by the HindIII enzyme.

In FIG. 19 lanes A, B and C correspond respectively to strains EL1016, EL1014 and EL1015. The letter "o" corresponds to the wild type of the threonine operon. Each of the other bands corresponds to one insertion of MudAM9.

In lane A only the "o" band corresponding to the threonine operon is shown. In lane B, 3 additional bands are shown numbered 1 to 3 and corresponding to at least 3 insertions of MudAM9. In lane C, 2 additional bands correspond to 2 insertions of MudAM9 at least.

TABLE XI

Copy number and production of L-threonine

| Strain | Copy number | Production of L-Thr (g/l) |
|---|---|---|
| EL1014 | 3 | 6.2 |
| EL1015 | 2 | 5.3 |

EXAMPLE 9

Stability of the Localization and Number of Defective Phages during Fermentation The strain EL1003 ($\lambda^+$, Pro$^-$) was transduced by a P1 phage cultured on a Pro$^+$ strain. A strain EL1003 ($\lambda^+$, Pro$^+$) was selected. The λ phage contained in this strain was then eliminated (C. Morel, personal communication). The strain thus obtained: EL1003 ($\lambda^+$, Pro$^+$) was designated EL1017.

The EL1017 strain containing 10 copies (at least) of MudAM9 was tested before and after fermentation in order to determine the stability of MudAM9 during this stage.

The fermenter containing 1.5 liters of fermentation medium (Example 2: components of the medium) was cultured with the EL1017 strain; the fermentation took place for 48 hours at the appropriate temperature. Clones were isolated after fermentation, and 4 clones were studied in particular: EL1017-a, EL1017-b, EL1017-c and EL1017-d.

The parent strain EL1017 and also the clones EL1017-a, EL1017-b, EL1017-c and EL1017-d were analyzed by the Southern DNA—DNA hybridization technique (Example 3) by which means it was possible to define the localization and the number of defective phages in the clones tested.

The chromosomal DNAs of strains EL1016 (Example 6), EL1017, EL1017-a, EL1017-b, EL1017-c and EL1017-d were extracted and then digested by the HindIII restriction enzyme.

Figures 20A, 20B, 20C, 20D, 20E, 20F:
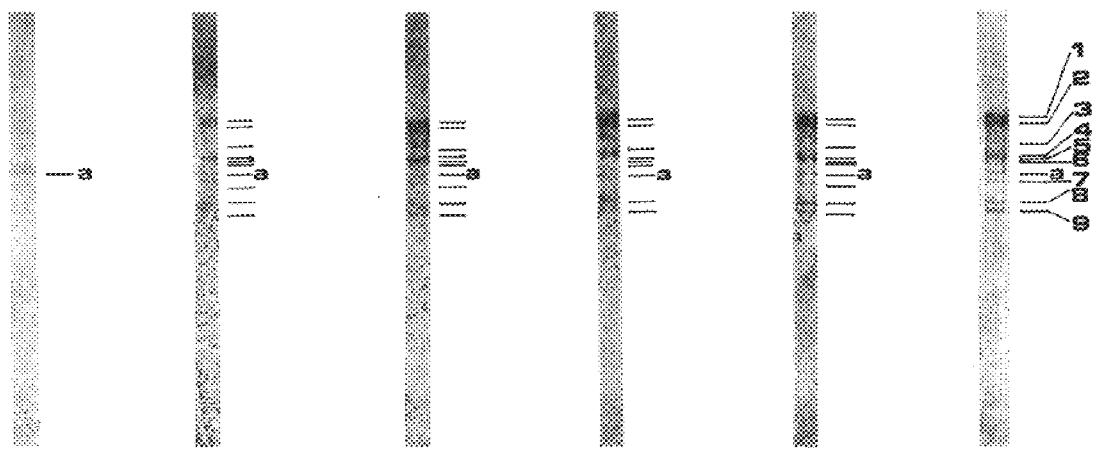
FIGS. 20A–20F: shows the results of electrophoresis followed by blot hybridization of the DNA of strains EL1016, EL1017, EL1017-a, EL1017-b, EL1017-c and EL1017-d for lanes A to F respectively (the probe is the EcoRI-HindIII fragment containing the genes nDtII, thra, thrE and thrC' of the pAM9 plasmid.

After electrophoresis, they were absorbed on nylon membrane and hybridized with the EcoRI-HindIII fragment labeled (by sulfonation) (containing the genes nptII, thra, thrB and thrC') of the pAN9 plasmid (FIG. 1). The result of the DNA—DNA hybridization is shown in FIG. 20.

Lanes A, B, C, D, E and F correspond respectively to strains EL1016, EL1017, EL1017-a, EL1017-b, EL1017-c and EL1017-d.

The letter "a" corresponds to the wild type of the threonine operon.

The numbers correspond to the bands marking the specificity of hybridization with MudAM9. One band corresponds to one insertion of MudAM9.

Lane A: Only the "a" band corresponding to the threonine operon is shown.

Lanes B, C, D, E and F: 10 bands (at least) are shown, the "a" band and 9 others numbered "1" to "9" corresponding to 9 insertions (at least) of MudAM9.

According to these results the hybridization profiles of the parent strain and the clones resulting from fermentation are similar. This reveals the stability of the defective phages inserted in the chromosomes of the bacteria used for the fermentation.

The following strains were deposited at the Collection Nationale de Cultures de Microorganismes, Institut Pasteur, 25 rue du Docteur-Roux, Paris (15th) on Jan. 25, 1988:

| | |
|---|---|
| *Escherichia coli* K12 POII1681 | under No. I-727 |
| *Escherichia coli* K12 POII1734 | under No. I-728 |
| *Escherichia coli* K12 EL1001 | under No. I-729 |

| Escherichia coli K12 EL1002 | under No. I-730 |
| Escherichia coli K12 EL1003 | under No. I-731. |

What is claimed is:

1. An *Escherichia coli* or *Erwinia chrysanthemi* strain having a chromosome comprising multiple stably integrated copies of a recombinant transposon, wherein said transposon is incapable of expressing a functional transposase and comprises, inserted therein, a chosen DNA molecule.

2. The bacterial strain of claim 1 wherein said recombinant transposon is from a Mu phage.

3. The bacterial strain of claim 2, wherein said Mu phage is MudI or MudII.

4. The bacterial strain of claim 1 wherein said recombinant transposon is Tn3, Tn5, Tn7, Tn10, Tn903, TnHoHo, IS 1, IS 10, IS 50 or a phage having the capacity to transpose.

5. The bacterial strain of claim 1 wherein said chosen DNA molecule comprises a chosen gene.

6. The bacterial strain of claim 5, wherein said chosen gene is a gene encoding a protein of the biosynthetic pathway of an amino acid.

7. The bacterial strain of claim 6, wherein said amino acid is L-threonine.

8. The bacterial strain of claim 6, wherein, relative to its parental strain, said strain is an over-producer of said amino acid.

9. The bacterial strain of claim 8, wherein said amino acid is L-threonine.

10. The bacterial strain of claim 1, wherein said chosen DNA molecule comprises an operon encoding a protein of the biosynthetic pathway of an amino acid.

11. The bacterial strain of claim 10, wherein said operon encodes a protein of the biosynthetic pathway of L-threonine.

12. An *Escherichia coli* or *Erwinia chrysanthemi* strain having an episome comprising multiple stably integrated copies of a recombinant transposon, wherein said transposon is incapable of expressing a functional transposase and comprises, inserted therein, a chosen DNA molecule.

13. The bacterial strain of claim 12, wherein said recombinant transposon is from a Mu phage.

14. The bacterial strain of claim 13 wherein said Mu phage is MudI or MudII.

15. The bacterial strain of claim 12, wherein said recombinant transposon is Tn3, Tn5, Tn7, Tn1O, Tn903, TnHoHo, IS 1, IS 10, IS 50 or a phage having the capacity to transpose.

16. The bacterial strain of claim 12, wherein said chosen DNA molecule comprises a chosen gene.

17. The bacterial strain of claim 12, wherein said chosen gene is a gene encoding a protein of the biosynthetic pathway of an amino acid.

18. The bacterial strain of claim 17, wherein said amino acid is L-threonine.

19. The bacterial strain of claim 17, wherein relative to its parental strain, said strain is an over-producer of said amino acid.

20. The bacterial strain of claim 19, wherein said amino acid is L-threonine.

21. The bacterial strain of claim 12, wherein said chosen DNA molecule comprises an operon encoding a protein of the biosynthetic pathway of an amino acid.

22. The bacterial strain of claim 21, wherein said operon encodes a protein of the biosynthetic pathway of L-threonine.

23. A method for producing an amino acid by fermentation comprising culturing a *Escherichia coli* or *Erwinia chrysanthemi* strain having a chromosome comprising multiple stably integrated copies of a recombinant transposon, wherein said transposon is incapable of expressing a functional transposase and comprises, inserted therein, a chosen DNA molecule comprising a gene encoding a protein of the biosynthetic pathway of said amino acid, under conditions in which said gene is expressed, whereby said amino acid is produced.

24. The method of claim 23, wherein said recombinant transposon is from a Mu phage.

25. The method of claim 24, wherein said Mu phage is MudI or MudII.

26. The method of claim 23, wherein said recombinant transposon is Tn3, Tn5, Tn7, Tn10, Tn903, TnHoHo, IS 1, IS 10, IS 50 or a phage having the capacity to transpose.

27. The method of claim 23 wherein said chosen DNA molecule comprises a chosen gene.

28. The method of claim 27, wherein said chosen gene is a gene encoding a protein of the biosynthetic pathway of an amino acid.

29. The method of claim 28, wherein said amino acid is L-threonine.

30. The method of claim 28, wherein, relative to its parental strain, said strain is an over-producer of said amino acid.

31. The method of claim 30, wherein said amino acid is L-threonine.

32. The method of claim 23, wherein said chosen DNA molecule comprises an operon encoding a protein of the biosynthetic pathway of an amino acid.

33. The method of claim 32, wherein said operon encodes a protein of the biosynthetic pathway of L-threonine.

34. A method for producing an amino acid by fermentation comprising culturing a *Escherichia coli* or *Erwinia chrysanthemi* strain having an episome comprising multiple stably integrated copies of a recombinant transposon, wherein said transposon is incapable of expressing a functional transposase and comprises, inserted therein, a chosen DNA molecule comprising a gene encoding a protein of the biosynthetic pathway of said amino acid, under conditions in which said gene is expressed whereby said amino acid is produced.

35. The method of claim 34, wherein said recombinant transposon is from a Mu phage.

36. The method of claim 35, wherein said Mu phage is MudI or MudII.

37. The method of claim 34, wherein said recombinant transposon is Tn3, Tn5, Tn7, Tn10, Tn903, TnHoHo, IS 1, IS 10, IS 50 or a phage having the capacity to transpose.

38. The method of claim 34, wherein said chosen DNA molecule comprises a chosen gene.

39. The method of claim 38, wherein said chosen gene is a gene encoding a protein of the biosynthetic pathway of an amino acid.

40. The method of claim 39, wherein said amino acid is L-threonine.

41. The method of claim 39, wherein relative to its parental strain, said strain is an over-producer of said amino acid.

42. The method of claim 41, wherein said amino acid is L-threonine.

43. The method of claim 34, wherein said chosen DNA molecule comprises an operon encoding a protein of the biosynthetic pathway of an amino acid.

44. The method of claim 43, wherein said operon encodes a protein of the biosynthetic pathway of L-threonine.

* * * * *

UNITED STATES PATENT AND TRADEMARK OFFICE
CERTIFICATE OF CORRECTION

PATENT NO.    : 6,197,590 B1
DATED         : March 6, 2001
INVENTOR(S)   : Richaud et al.

It is certified that error appears in the above-identified patent and that said Letters Patent is hereby corrected as shown below:

Column 2,
Line 47, change "TnlO" to -- Tn10 --;

Column 21,
Line 2, change "TnlO" to -- Tn10 --.

Signed and Sealed this

Seventh Day of May, 2002

Attest:

Attesting Officer

JAMES E. ROGAN
Director of the United States Patent and Trademark Office